(12) United States Patent  
von Deyn et al.

(10) Patent No.: US 7,196,229 B2
(45) Date of Patent: Mar. 27, 2007

(54) BENZOYLCYCLOHEXENONE DERIVATIVES

(75) Inventors: Wolfgang von Deyn, Neustadt (DE); Ernst Baumann, Dudenhofen (DE); Michael Hofmann, Ludwigshafen (DE); Markus Kordes, Frankenthal (DE); Ulf Misslitz, Neustadt (DE); Liliana Parra Rapado, Mannheim (DE); Cyrill Zagar, Mannheim (DE); Matthias Witschel, Bad Dürkheim (DE); Andreas Landes, Römerberg Heiligenstein (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 10/485,922

(22) PCT Filed: Jul. 26, 2002

(86) PCT No.: PCT/EP02/08320

§ 371 (c)(1),
(2), (4) Date: Feb. 5, 2004

(87) PCT Pub. No.: WO03/014071

PCT Pub. Date: Feb. 20, 2003

(65) Prior Publication Data

US 2004/0235793 A1 Nov. 25, 2004

(30) Foreign Application Priority Data

Aug. 8, 2001 (DE) ................. 101 37 049

(51) Int. Cl.
C07C 315/00 (2006.01)

(52) U.S. Cl. ............................ 568/31; 568/37; 568/42; 568/43; 564/440; 558/412

(58) Field of Classification Search .............. 568/31, 568/37, 42, 43; 564/440; 558/412
See application file for complete search history.

(56) References Cited

U.S. PATENT DOCUMENTS

| 4,762,551 | A | * | 8/1988 | Knudsen | 504/348 |
| 4,775,411 | A | * | 10/1988 | Knudsen | 504/326 |
| 4,797,150 | A | * | 1/1989 | Carter | 504/310 |
| 4,837,352 | A | * | 6/1989 | Knudsen | 558/396 |
| 5,228,898 | A | * | 7/1993 | Ueda et al. | 504/189 |
| 5,468,905 | A | * | 11/1995 | Suzuki et al. | 568/346 |

FOREIGN PATENT DOCUMENTS

| DE | 3902818 A1 | * | 8/1989 |
| EP | 186 120 | | 7/1986 |
| EP | 0 249 813 A1 | * | 12/1987 |
| EP | 249 813 | | 12/1987 |
| EP | 319 975 | | 6/1989 |
| GB | 2 215 333 | | 9/1989 |
| GB | 2215333 | * | 9/1989 |

* cited by examiner

*Primary Examiner*—Thurman K. Page
*Assistant Examiner*—Chukwuma Nwaonicha
(74) *Attorney, Agent, or Firm*—Novak, Druce & Quigg, LLP

(57) ABSTRACT

The invention relates to benzoylcyclohexenone derivatives of general formula (I) wherein the variables $R^1$ to $R^{10}$ and n have the designation cited in claim 1. The invention also relates to the salts of the same and the use of said derivatives for controlling harmful plants

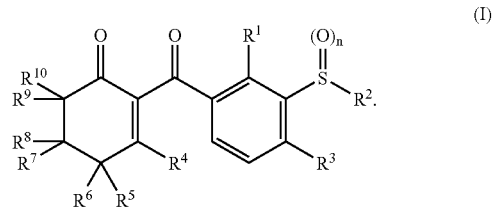

25 Claims, No Drawings

BENZOYLCYCLOHEXENONE DERIVATIVES

The present invention relates to benzoylcyclohexenone derivatives and their agriculturally acceptable salts, to processes for their preparation, to compositions comprising such compounds and to the use of the benzoylcyclohexenone derivatives, their salts and/or compositions comprising them for controlling harmful plants.

Trisubstituted benzoylcyclohexenones are described in the prior art as herbicidally active compounds.

Thus, EP 186 120 describes herbicidally active compounds of the formula A

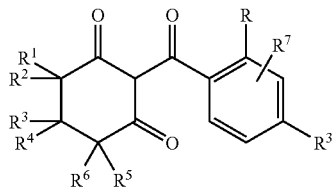

in which, inter alia,
R is $C_1$–$C_4$-alkyl or $C_1$–$C_4$-haloalkyl,
$R^1$, $R^2$, $R^3$, $R^4$, $R^5$, $R^6$ can be hydrogen or $C_1$–$C_4$-alkyl and
$R^7$, $R^8$ independently of one another are, inter alia, halogen, $C_1$–$C_4$-alkyl, $C_1$–$C_4$-alkoxy, $OCF_3$, cyano, nitro, $C_1$–$C_4$-haloalkyl or a radical of the formula $R^bSO_n$ in which $R^b$ is $C_1$–$C_4$-alkyl and n is 0, 1 or 2.
$R^7$ is in particular hydrogen.

Furthermore, EP 0 319 075 discloses benzoylcyclohexenone derivatives of the formula B

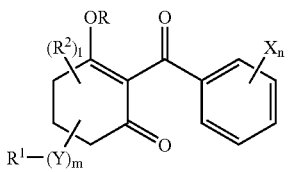

in which
X can be identical or different and is, inter alia, halogen, nitro, cyano, alkyl, haloalkyl, alkylthio, haloalkylthio, alkylsulfonyl, haloalkylsulfonyl, alkylsulfinyl, haloalkylsulfinyl,
R is, inter alia, hydrogen or alkyl,
$R^1$ is hydroxyl, cyano, nitro, alkylcarbonyl,
$R^2$ is, inter alia, alkyl,
Y is alkylene,
n and l are 0, 1, 2, 3, 4 or 5 and
m is 0 or 1.

Moreover, EP 249 150 discloses 2-benzoylcyclohex-2-enones where the cyclohex-2-enone radical is attached in the 3-position to a thio substituent.

The activity against harmful plants of the benzoylcyclohexenones known from the prior art is often unsatisfactory. In addition, these compounds are frequently not compatible with crop plants but act unselectively against useful and harmful plants.

It is an object of the present invention to provide novel herbicides which allow better control of harmful plants. The novel herbicides should advantageously have high activity against harmful plants. Moreover, compatibility with crop plants is desirable.

We have found that this object is surprisingly achieved by benzoylcyclohexenone derivatives of the formula I defined below.

Accordingly, the present invention relates to benzoylcyclohexenone derivatives of the formula I

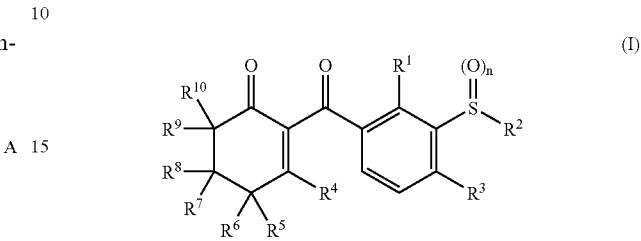

in which the variables are as defined below:
$R^1$ is $C_1$–$C_6$-alkyl, $C_1$–$C_6$-haloalkyl or $C_1$–$C_4$-alkoxy-$C_1$–$C_4$-alkyl;
$R^2$ is $C_1$–$C_6$-alkyl or $C_1$–$C_6$-haloalkyl;
$R^3$ is halogen, cyano, nitro, $C_1$–$C_6$-alkyl, $C_1$–$C_6$-haloalkyl, $C_1$–$C_6$-alkoxy, $C_1$–$C_6$-haloalkoxy, $C_1$–$C_6$-alkylthio, $C_1$–$C_6$-haloalkylthio, $C_1$–$C_6$-alkylsulfinyl, $C_1$–$C_6$-haloalkylsulfinyl, $C_1$–$C_6$-alkylsulfonyl or $C_1$–$C_6$-haloalkylsulfonyl;
$R^4$ is hydroxyl, $SR^{11}$ or $NR^{12}R^{13}$;
$R^5$, $R^6$, $R^9$, $R^{10}$ independently of one another are hydrogen or $C_1$–$C_4$-alkyl;
$R^7$, $R^8$ independently of one another are hydrogen or $C_1$–$C_4$-alkyl or together with the carbon atom to which they are attached form a carbonyl group;
n is 0, 1 or 2;
where
$R^{11}$ is $C_1$–$C_4$-alkyl or phenyl which may be partially or fully halogenated and/or or may carry one to three of the following groups: nitro, cyano, $C_1$–$C_4$-alkyl, $C_1$–$C_4$-haloalkyl, $C_1$–$C_4$-alkoxy or $C_1$–$C_4$-haloalkoxy;
$R^{12}$ is hydrogen, $C_1$–$C_4$-alkyl or $C_1$–$C_4$-alkoxy;
$R^{13}$ is hydrogen or $C_1$–$C_4$-alkyl;
or
$R^{12}$ and $R^{13}$ together with the nitrogen to which they are attached are a 5- or 6-membered saturated, partially saturated or unsaturated nitrogen heterocycle which may have one or two further heteroatoms selected from the group consisting of O, S and N and which may be partially or fully halogenated and/or may carry one, two or three of the following radicals: cyano, $C_1$–$C_4$-alkyl, $C_1$–$C_4$-haloalkyl, $C_1$–$C_4$-alkoxy or $C_1$–$C_4$-haloalkoxy;
and its agriculturally useful salts.

The invention furthermore relates to processes for preparing the benzoylcyclohexenone derivatives of the formula I, to herbicidal compositions comprising the benzoylcyclohexenone derivatives of the formula I and to methods for controlling undesirable vegetation using the benzoylcyclohexenone derivatives of the formula I.

Depending on the nature of the substituents, the compounds of the formula I may contain one or more centers of chirality, in which case they are present as enantiomers or mixtures of diastereomers. The invention provides both the pure enantiomers or diastereomers and their mixtures.

The compounds of the formula I can also be employed in the form of their agriculturally useful salts, the type of salt generally being immaterial, as long as it is agriculturally acceptable.

In general, the salts of those cations or the acid addition salts of those acids are used whose cations and anions, respectively, have no adverse effect on the herbicidal action of the compounds I.

Suitable cations are in particular ions of the alkali metals, preferably lithium, sodium and potassium, of the alkaline earth metals, preferably calcium and magnesium, and of the transition metals, preferably manganese, copper, zinc and iron, and also ammonium, where, if desired, one to four hydrogen atoms may be replaced by $C_1$–$C_4$-alkyl, hydroxy-$C_1$–$C_4$-alkyl, $C_1$–$C_4$-alkoxy-$C_1$–$C_4$-alkyl, hydroxy-$C_1$–$C_4$-alkoxy-$C_1$–$C_4$-alkyl, phenyl or benzyl, preferably ammonium, dimethylammonium, diisopropylammonium, tetramethylammonium, tetrabutylammonium, 2-(2-hydroxyeth-1-oxy)eth-1-ylammonium, di-(2-hydroxyeth-1-yl)ammonium, trimethylbenzylammonium, furthermore phosphonium ions, sulfonium ions, preferably tri($C_1$–$C_4$-alkyl)sulfonium, and sulfoxonium ions, preferably tri($C_1$–$C_4$-alkyl)sulfoxonium.

Anions of useful acid addition salts are primarily chloride, bromide, fluoride, hydrogensulfate, sulfate, dihydrogenphosphate, hydrogenphosphate, nitrate, bicarbonate, carbonate, hexafluorosilicate, hexafluorophosphate, benzoate, and also the anions of $C_1$–$C_4$-alkanoic acids, preferably formate, acetate, propionate and butyrate.

In the case of $R^4$=hydroxyl, in the formula I the cyclohexenone moiety of the formula II attached in the 2-position also represents the tautomeric forms IIa, IIb and IIc in which the radicals $R^5$, $R^6$, $R^7$, $R^8$, $R^9$ and $R^{10}$ are as defined above.

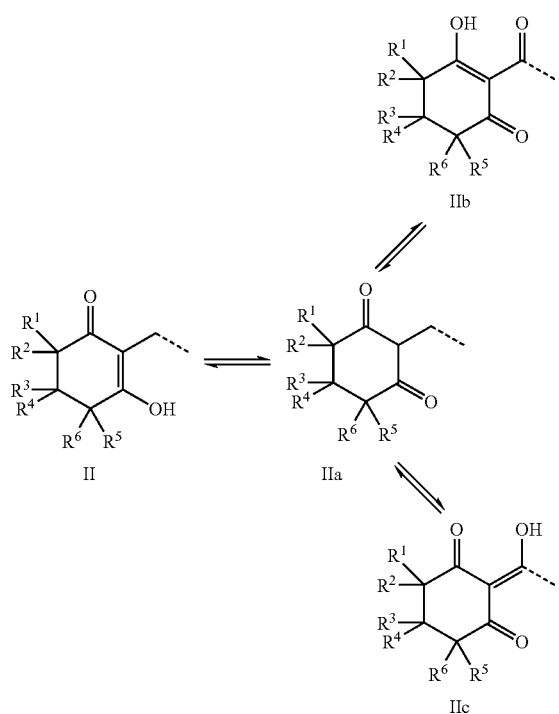

The organic moieties mentioned for the substituents $R^1$ to $R^{13}$ or as radicals on phenyl or heterocyclyl radicals are collective terms for individual enumerations of the individual group members. All hydrocarbon chains, i.e. all alkyl, haloalkyl, alkoxy, haloalkoxy, hydroxyalkyl, alkoxyalkyl, hydroxyalkoxyalkyl, alkylthio, haloalkylthio, alkylsulfinyl, haloalkylsulfinyl, alkylsulfonyl, haloalkylsulfonyl, trialkylsulfonium and trialkylsulfoxonium moieties can be straight-chain or branched. The term halogen denotes in each case fluorine, chlorine, bromine or iodine.

Examples of other meanings are:

$C_1$–$C_4$-alkyl and the alkyl moieties of hydroxy-$C_1$–$C_4$-alkyl, tri($C_1$–$C_4$-alkyl)sulfonium and tri($C_1$–$C_4$-alkyl)sulfoxonium: for example methyl, ethyl, propyl, 1-methylethyl, butyl, 1-methylpropyl, 2-methylpropyl and 1,1-dimethylethyl;

$C_1$–$C_6$-alkyl: $C_1$–$C_4$-alkyl as mentioned above and also, for example, n-pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1-ethyl-1-methylpropyl and 1-ethyl-3-methylpropyl;

$C_1$–$C_4$-haloalkyl: a $C_1$–$C_4$-alkyl radical as mentioned above which is partially or fully substituted by fluorine, chlorine, bromine and/or iodine, i.e., for example, chloromethyl, dichloromethyl, trichloromethyl, fluoromethyl, difluoromethyl, trifluoromethyl, chlorofluoromethyl, dichlorofluoromethyl, chlorodifluoromethyl, 2-fluoroethyl, 2-chloroethyl, 2-bromoethyl, 2-iodoethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl, 2-fluoropropyl, 3-fluoropropyl, 2,2-difluoropropyl, 2,3-difluoropropyl, 2-chloropropyl, 3-chloropropyl, 2,3-dichloropropyl, 2-bromopropyl, 3-bromopropyl, 3,3,3-trifluoropropyl, 3,3,3-trichloropropyl, 2,2,3,3,3-pentafluoropropyl, heptafluoropropyl, 1-(fluoromethyl)-2-fluoroethyl, 1-(chloromethyl)-2-chloroethyl, 1-(bromomethyl)-2-bromoethyl, 4-fluorobutyl, 4-chlorobutyl, 4-bromobutyl or nonafluorobutyl;

$C_1$–$C_6$-haloalkyl: $C_1$–$C_4$-haloalkyl as mentioned above and also, for example, 5-fluoropentyl, 5-chloropentyl, 5-bromopentyl, 5-iodopentyl, undecafluoropentyl, 6-fluorohexyl, 6-chlorohexyl, 6-bromohexyl, 6-iodohexyl and dodecafluorohexyl;

$C_1$–$C_4$-alkoxy: for example methoxy, ethoxy, propoxy, 1-methylethoxy, butoxy, 1-methylpropoxy, 2-methylpropoxy and 1,1-dimethylethoxy;

$C_1$–$C_6$-alkoxy: $C_1$–$C_4$-alkoxy as mentioned above and also, for example, pentoxy, 1-methylbutoxy, 2-methylbutoxy, 3-methylbutoxy, 1,1-dimethylpropoxy, 1,2-dimethylpropoxy, 2,2-dimethylpropoxy, 1-ethylpropoxy, hexoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy and 1-ethyl-2-methylpropoxy;

$C_1$–$C_4$-alkoxy-$C_1$–$C_4$-alkyl and the alkoxyalkyl moieties of hydroxy-$C_1$–$C_4$-alkoxy-$C_1$–$C_4$-alkyl: $C_1$–$C_4$-alkyl which is substituted by $C_1$–$C_4$-alkoxy as mentioned above, i.e., for example, methoxymethyl, ethoxymethyl, propoxymethyl, (1-methylethoxy)methyl, butoxymethyl, (1-methylpropoxy)methyl, (2-methylpropoxy)methyl, (1,1-dimethylethoxy)methyl, 2-(methoxy)ethyl, 2-(ethoxy)ethyl, 2-(propoxy)ethyl, 2-(1-methylethoxy)ethyl, 2-(butoxy)ethyl, 2-(1-methylpropoxy)ethyl, 2-(2-methylpropoxy)

ethyl, 2-(1,1-dimethylethoxy)ethyl, 2-(methoxy)-propyl, 2-(ethoxy)propyl, 2-(propoxy)propyl, 2-(1-methylethoxy) propyl, 2-(butoxy)propyl, 2-(1-methylpropoxy)propyl, 2-(2-methylpropoxy)propyl, 2-(1,1-dimethylethoxy)propyl, 3-(methoxy)propyl, 3-(ethoxy)propyl, 3-(propoxy) propyl, 3-(1-methylethoxy)propyl, 3-(butoxy)propyl, 3-(1-methylpropoxy)propyl, 3-(2-methylpropoxy)propyl, 3-(1,1-dimethylethoxy)propyl, 2-(methoxy)butyl, 2-(ethoxy)butyl, 2-(propoxy)butyl, 2-(1-methylethoxy) butyl, 2-(butoxy)butyl, 2-(1-methylpropoxy)butyl, 2-(2-methylpropoxy)butyl, 2-(1,1-dimethylethoxy)butyl, 3-(methoxy)butyl, 3-(ethoxy)butyl, 3-(propoxy)butyl, 3-(1-methylethoxy)butyl, 3-(butoxy)butyl, 3-(1-methylpropoxy)butyl, 3-(2-methylpropoxy)butyl, 3-(1,1-dimethylethoxy)butyl, 4-(methoxy)butyl, 4-(ethoxy)butyl, 4-(propoxy)butyl, 4-(1-methylethoxy)butyl, 4-(butoxy) butyl, 4-(1-methylpropoxy)butyl, 4-(2-methylpropoxy) butyl and 4-(1,1-dimethylethoxy)butyl;

$C_1$–$C_4$-haloalkoxy: a $C_1$–$C_4$-alkoxy radical as mentioned above which is partially or fully substituted by fluorine, chlorine, bromine and/or iodine, i.e., for example, fluoromethoxy, difluoromethoxy, trifluoromethoxy, chlorodifluoromethoxy, bromodifluoromethoxy, 2-fluoroethoxy, 2-chloroethoxy, 2-bromomethoxy, 2-iodoethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy, pentafluoroethoxy, 2-fluoropropoxy, 3-fluoropropoxy, 2-chloropropoxy, 3-chloropropoxy, 2-bromopropoxy, 3-bromopropoxy, 2,2-difluoropropoxy, 2,3-difluoropropoxy, 2,3-dichloropropoxy, 3,3,3-trifluoropropoxy, 3,3,3-trichloropropoxy, 2,2,3,3,3-pentafluoropropoxy, heptafluoropropoxy, 1-(fluoromethyl)-2-fluoroethoxy, 1-(chloromethyl)-2-chloroethoxy, 1-(bromomethyl)-2-bromoethoxy, 4-fluorobutoxy, 4-chlorobutoxy, 4-bromobutoxy or nonafluorobutoxy;

$C_1$–$C_6$-haloalkoxy: $C_1$–$C_4$-haloalkoxy as mentioned above and also, for example, 5-fluoropentoxy, 5-chloropentoxy, 5-bromopentoxy, 5-iodopentoxy, undecafluoropentoxy, 6-fluorohexoxy, 6-chlorohexoxy, 6-bromohexoxy, 6-iodohexoxy or dodecafluorohexoxy;

$C_1$–$C_6$-alkylthio ($C_1$–$C_6$-alkylsulfanyl: $C_1$–$C_6$-alkyl-S—): for example methylthio, ethylthio, propylthio, 1-methylethylthio, butylthio, 1-methylpropylthio, 2-methylpropylthio or 1,1-dimethylethylthio, pentylthio, 1-methylbutylthio, 2-methylbutylthio, 3-methylbutylthio, 2,2-dimethylpropylthio, 1-ethylpropylthio, hexylthio, 1,1-dimethylpropylthio, 1,2-dimethylpropylthio, 1-methylpentylthio, 2-methylpentylthio, 3-methylpentylthio, 4-methylpentylthio, 1,1-dimethylbutylthio, 1,2-dimethylbutylthio, 1,3-dimethylbutylthio, 2,2-dimethylbutylthio, 2,3-dimethylbutylthio, 3,3-dimethylbutylthio, 1-ethylbutylthio, 2-ethylbutylthio, 1,1,2-trimethylpropylthio, 1,2,2-trimethylpropylthio, 1-ethyl-1-methylpropylthio and 1-ethyl-2-methylpropylthio;

$C_1$–$C_6$-haloalkylthio: a $C_1$–$C_6$-alkylthio radical as mentioned above which is partially or fully substituted by fluorine, chlorine, bromine and/or iodine, i.e., for example, fluoromethylthio, difluoromethylthio, trifluoromethylthio, chlorodifluoromethylthio, bromodifluoromethylthio, 2-fluoroethylthio, 2-chloroethylthio, 2-bromoethylthio, 2-iodoethylthio, 2,2-difluoroethylthio, 2,2,2-trifluoroethylthio, 2,2,2-trichloroethylthio, 2-chloro-2-fluoroethylthio, 2-chloro-2,2-difluoroethylthio, 2,2-dichloro-2-fluoroethylthio, pentafluoroethylthio, 2-fluoropropylthio, 3-fluoropropylthio, 2-chloropropylthio, 3-chloropropylthio, 2-bromopropylthio, 3-bromopropylthio, 2,2-difluoropropylthio, 2,3-difluoropropylthio, 2,3-dichloropropylthio, 3,3,3-trifluoropropylthio, 3,3,3-trichloropropylthio, 2,2,3,3,3-pentafluoropropylthio, heptafluoropropylthio, 1-(fluoromethyl)-2-fluoroethylthio, 1-(chloromethyl)-2-chloroethylthio, 1-(bromomethyl)-2-bromoethylthio, 4-fluorobutylthio, 4-chlorobutylthio, 4-bromobutylthio, nonafluorobutylthio, 5-fluoropentylthio, 5-chloropentylthio, 5-bromopentylthio, 5-iodopentylthio, undecafluoropentylthio, 6-fluorohexylthio, 6-chlorohexylthio, 6-bromohexylthio, 6-iodohexylthio and dodecafluorohexylthio;

$C_1$–$C_6$-alkylsulfinyl ($C_1$–$C_6$-alkyl-S(=O)—): for example methylsulfinyl, ethylsulfinyl, propylsulfinyl, 1-methylethylsulfinyl, butylsulfinyl, 1-methylpropylsulfinyl, 2-methylpropylsulfinyl or 1,1-dimethylethylsulfinyl, pentylsulfinyl, 1-methylbutylsulfinyl, 2-methylbutylsulfinyl, 3-methylbutylsulfinyl, 2,2-dimethylpropylsulfinyl, 1-ethylpropylsulfinyl, 1,1-dimethylpropylsulfinyl, 1,2-dimethylpropylsulfinyl, hexylsulfinyl, 1-methylpentylsulfinyl, 2-methylpentylsulfinyl, 3-methylpentylsulfinyl, 4-methylpentylsulfinyl, 1,1-dimethylbutylsulfinyl, 1,2-dimethylbutylsulfinyl, 1,3-dimethylbutylsulfinyl, 2,2-dimethylbutylsulfinyl, 2,3-dimethylbutylsulfinyl, 3,3-dimethylbutylsulfinyl, 1-ethylbutylsulfinyl, 2-ethylbutylsulfinyl, 1,1,2-trimethylpropylsulfinyl, 1,2,2-trimethylpropylsulfinyl, 1-ethyl-1-methylpropylsulfinyl or 1-ethyl-2-methylpropylsulfinyl;

$C_1$–$C_6$-haloalkylsulfinyl: a $C_1$–$C_6$-alkylsulfinyl radical as mentioned above which is partially or fully substituted by fluorine, chlorine, bromine and/or iodine, i.e., for example, fluoromethylsulfinyl, difluoromethylsulfinyl, trifluoromethylsulfinyl, chlorodifluoromethylsulfinyl, bromodifluoromethylsulfinyl, 2-fluoroethylsulfinyl, 2-chloroethylsulfinyl, 2-bromoethylsulfinyl, 2-iodoethylsulfinyl, 2,2-difluoroethylsulfinyl, 2,2,2-trifluoroethylsulfinyl, 2,2,2-trichloroethylsulfinyl, 2-chloro-2-fluoroethylsulfinyl, 2-chloro-2,2-difluoroethylsulfinyl, 2,2-dichloro-2-fluoroethylsulfinyl, pentafluoroethylsulfinyl, 2-fluoropropylsulfinyl, 3-fluoropropylsulfinyl, 2-chloropropylsulfinyl, 3-chloropropylsulfinyl, 2-bromopropylsulfinyl, 3-bromopropylsulfinyl, 2,2-difluoropropylsulfinyl, 2,3-difluoropropylsulfinyl, 2,3-dichloropropylsulfinyl, 3,3,3-trifluoropropylsulfinyl, 3,3,3-trichloropropylsulfinyl, 2,2,3,3,3-pentafluoropropylsulfinyl, heptafluoropropylsulfinyl, 1-(fluoromethyl)-2-fluoroethylsulfinyl, 1-(chloromethyl)-2-chloroethylsulfinyl, 1-(bromomethyl)-2-bromoethylsulfinyl, 4-fluorobutylsulfinyl, 4-chlorobutyl-sulfinyl, 4-bromobutylsulfinyl, nonafluorobutylsulfinyl, 5-fluoropentylsulfinyl, 5-chloropentylsulfinyl, 5-bromopentylsulfinyl, 5-iodopentylsulfinyl, undecafluoropentylsulfinyl, 6-fluorohexylsulfinyl, 6-chlorohexylsulfinyl, 6-bromohexylsulfinyl, 6-iodohexylsulfinyl and dodecafluorohexylsulfinyl;

$C_1$–$C_6$-alkylsulfonyl ($C_1$–$C_6$-alkyl-S(=O)$_2$—): for example methylsulfonyl, ethylsulfonyl, propylsulfonyl, 1-methylethylsulfonyl, butylsulfonyl, 1-methylpropylsulfonyl, 2-methylpropylsulfonyl, 1,1-dimethylethylsulfonyl, pentylsulfonyl, 1-methylbutylsulfonyl, 2-methylbutylsulfonyl, 3-methylbutylsulfonyl, 1,1-dimethylpropylsulfonyl, 1,2-dimethylpropylsulfonyl, 2,2-dimethylpropylsulfonyl, 1-ethylpropylsulfonyl, hexylsulfonyl, 1-methylpentylsulfonyl, 2-methylpentylsulfonyl, 3-methylpentylsulfonyl, 4-methylpentylsulfonyl, 1,1-dimethylbutylsulfonyl, 1,2-dimethylbutylsulfonyl, 1,3-dimethylbutylsulfonyl, 2,2-dimethylbutylsulfonyl, 2,3-dimethylbutylsulfonyl, 3,3-dimethylbutylsulfonyl, 1-ethylbutylsulfonyl, 2-ethylbutylsulfonyl, 1,1,2-trimethylpropylsulfonyl, 1,2,2-trimethylpropylsulfonyl, 1-ethyl-1-methylpropylsulfonyl and 1-ethyl-2-methylpropylsulfonyl;

$C_1$–$C_6$-haloalkylsulfonyl: a $C_1$–$C_6$-alkylsulfonyl radical as mentioned above which is partially or fully substituted by fluorine, chlorine, bromine and/or iodine, i.e., for example, fluoromethylsulfonyl, difluoromethylsulfonyl, trifluoromethylsulfonyl, chlorodifluoromethylsulfonyl, bromodifluoromethylsulfonyl, 2-fluoroethylsulfonyl, 2-chloroethylsulfonyl, 2-bromoethylsulfonyl, 2-iodoethylsulfonyl, 2,2-difluoroethylsulfonyl, 2,2,2-trifluoroethylsulfonyl, 2-chloro-2-fluoroethylsulfonyl, 2-chloro-2,2-difluoroethylsulfonyl, 2,2-dichloro-2-fluoroethylsulfonyl, 2,2,2-trichloroethylsulfonyl, pentafluoroethylsulfonyl, 2-fluoropropylsulfonyl, 3-fluoropropylsulfonyl, 2-chloropropylsulfonyl, 3-chloropropylsulfonyl, 2-bromopropylsulfonyl, 3-bromopropylsulfonyl, 2,2-difluoropropylsulfonyl, 2,3-difluoropropylsulfonyl, 2,3-dichloropropylsulfonyl, 3,3,3-trifluoropropylsulfonyl, 3,3,3-trichloropropylsulfonyl, 2,2,3,3,3-pentafluoropropylsulfonyl, heptafluoropropylsulfonyl, 1-(fluoromethyl)-2-fluoroethylsulfonyl, 1-(chloromethyl)-2-chloroethylsulfonyl, 1-(bromomethyl)-2-bromoethylsulfonyl, 4-fluorobutylsulfonyl, 4-chlorobutylsulfonyl, 4-bromobutylsulfonyl, nonafluorobutylsulfonyl, 5-fluoropentylsulfonyl, 5-chloropentylsulfonyl, 5-bromopentylsulfonyl, 5-iodopentylsulfonyl, 6-fluorohexylsulfonyl, 6-bromohexylsulfonyl, 6-iodohexylsulfonyl and dodecafluorohexylsulfonyl.

Examples which may be mentioned for a 5- or 6-membered nitrogen heterocycle which may be saturated, partially unsaturated or unsaturated and may contain one or two further heteroatoms selected from the group consisting of nitrogen, oxygen and sulfur are:

5-membered rings such as:
tetrahydropyrrol-1-yl, 2,3-dihydro-1H-pyrrol-1-yl, 2,5-dihydro-1H-pyrrol-1-yl, pyrrol-1-yl, tetrahydropyrazol-1-yl, tetrahydroisoxazol-2-yl, tetrahydroisothiazol-2-yl, tetrahydroimidazol-1-yl, tetrahydrooxazol-3-yl, tetrahydrothiazol-3-yl, 4,5-dihydro-1H-pyrazol-1-yl, 2,5-dihydro-1H-pyrazol-1-yl, 2,3-dihydro-1H-pyrazol-1-yl, 2,5-dihydroisoxazol-2-yl, 2,3-dihydroisoxazol-2-yl, 2,5-dihydroisothiazol-2-yl, 2,3-dihydroisoxazol-2-yl, 4,5-dihydro-1H-imidazol-1-yl, 2,5-dihydro-1H-imidazol-1-yl, 2,3-dihydro-1H-imidazol-1-yl, 2,3-dihydrooxazol-3-yl, 2,3-dihydrothiazol-3-yl, pyrazol-1-yl, imidazol-1-yl, 1,2,4-$\Delta^4$-oxadiazolin-2-yl, 1,2,4-$\Delta^2$-oxadiazolin-4-yl, 1,2,4-$\Delta^3$-oxadiazolin-2-yl, 1,3,4-$\Delta^2$-oxadiazolin-4-yl, 1,2,4-$\Delta^5$-thiadiazolin-2-yl, 1,2,4-$\Delta^3$-thiadiazolin-2-yl, 1,2,4-$\Delta^2$-thiadiazolin-4-yl, 1,3,4-$\Delta^2$-thiadiazolin-2-yl, 1,2,4-$\Delta^2$-thiadiazolin-4-yl, 1,3,4-$\Delta^2$-thiadiazolin-4-yl, 1,2,3-$\Delta^2$-triazolin-1-yl, 1,2,4-$\Delta^2$-triazolin-1-yl, 1,2,4-$\Delta^2$-triazolin-4-yl, 1,2,4-$\Delta^3$-triazolin-1-yl, 1,2,4-$\Delta^1$-triazolin-4-yl, 1,2,3-triazol-1-yl, 1,2,4-triazol-1-yl or 1,3,4-triazol-1-yl;

6-membered rings such as:
Piperidin-1-yl, 1,2,3,4-tetrahydropyridin-1-yl, 1,2,5,6-tetrahydropyridin-1-yl, 1,4-dihydropyridin-1-yl, 1,2-dihydropyridin-1-yl, hexahydropyrimidin-1-yl, hexahydropyrazin-1-yl, hexahydropyridazin-1-yl, tetrahydro-1,3-oxazin-3-yl, tetrahydro-1,3-thiazin-3-yl, tetrahydro-1,4-thiazin-4-yl, tetrahydro-1,4-oxazin-4-yl (morpholinyl), tetrahydro-1,2-oxazin-2-yl, 2H-5,6-dihydro-1,2-oxazin-2-yl, 2H-5,6-dihydro-1,2-thiazin-2-yl, 2H-3,6-dihydro-1,2-oxazin-2-yl, 2H-3,6-dihydro-1,2-thiazin-2-yl, 2H-3,4-dihydro-1,2-thiazin-2-yl, 2,3,4,5-tetrahydropyridazin-2-yl, 1,2,5,6-tetrahydropyridazin-1-yl, 1,2,5,6-tetrahydropyridazin-2-yl, 1,2,3,6-tetrahydropyridazin-1-yl, 3,4,5,6-tetrahydropyrimidin-3-yl, 1,2,3,4-tetrahydropyrazin-1-yl, 1,2,3,4-tetrahydropyrimidin-1-yl, 1,2,3,4-tetrahydropyrimidin-3-yl, 2,3-dihydro-1,4-thiazin-4-yl, 2H-1,2-oxazin-2-yl, 2H-1,2-thiazin-2-yl, 4H-1,4-oxazin-4-yl, 4H-1,4-thiazin-4-yl, 1,4-dihydropyridazin-1-yl, 1,4-dihydropyrazin-1-yl, 1,2-dihydropyrazin-1-yl, 1,4-dihydropyrimidin-1-yl or 3,4-dihydropyrimidin-3-yl.

With a view to the use of the compounds of the formula I according to the invention as herbicides, the variables $R^1$ to $R^{13}$ are preferably as defined below, in each case on their own or in combination:

$R^1$ is $C_1$–$C_4$-alkyl, in particular methyl, ethyl or n-propyl, $C_1$–$C_4$-haloalkyl, in particular trifluoromethyl or difluoromethyl, or $C_1$–$C_2$-alkoxy-$C_1$–$C_2$-alkyl, in particular methoxymethyl or ethoxymethyl;

$R^2$ is $C_1$–$C_4$-alkyl, such as methyl, ethyl or n-propyl, or $C_1$–$C_4$-haloalkyl, such as trifluoromethyl or difluoromethyl;

$R^3$ is halogen, in particular fluorine, chlorine or bromine, cyano, nitro, $C_1$–$C_4$-alkoxy, such as, for example, methoxy, ethoxy or n-propoxy, $C_1$–$C_4$-haloalkoxy, in particular difluoromethoxy or trifluoromethoxy, $C_1$–$C_4$-alkylthio, in particular methylthio, ethylthio or n-propylthio, $C_1$–$C_4$-haloalkylthio, in particular difluoromethylthio or trifluoromethylthio, $C_1$–$C_4$-alkylsulfinyl, in particular methylsulfinyl, ethylsulfinyl or n-propylsulfinyl, $C_1$–$C_4$-haloalkylsulfinyl, in particular difluoromethylsulfinyl or trifluoromethylsulfinyl, $C_1$–$C_4$-alkylsulfonyl, in particular methylsulfonyl, ethylsulfonyl or n-propylsulfonyl, $C_1$–$C_4$-haloalkylsulfonyl, in particular difluoromethylsulfonyl or trifluoromethylsulfonyl; especially halogen, in particular fluorine, chlorine or bromine, cyano, nitro, $C_1$–$C_4$-alkoxy, such as, for example, methoxy, ethoxy or n-propoxy, $C_1$–$C_4$-alkylthio, in particular methylthio, ethylthio or n-propylthio, $C_1$–$C_4$-haloalkylthio, in particular difluoromethylthio or trifluoromethylthio, $C_1$–$C_4$-alkylsulfinyl, in particular methylsulfinyl, ethylsulfinyl or n-propylsulfinyl, $C_1$–$C_4$-haloalkylsulfinyl, in particular difluoromethylsulfinyl or trifluoromethylsulfinyl, $C_1$–$C_4$-alkylsulfonyl, in particular methylsulfonyl, ethylsulfonyl or n-propylsulfonyl, $C_1$–$C_4$-haloalkylsulfonyl, in particular difluoromethylsulfonyl or trifluoromethylsulfonyl;

$R^4$ is hydroxyl, $NR^{12}R^{13}$ or phenylthio, where the phenyl radical may be partially or fully halogenated and/or may carry one to three of the following groups: nitro, cyano, $C_1$–$C_4$-alkyl, $C_1$–$C_4$-haloalkyl, $C_1$–$C_4$-alkoxy or $C_1$–$C_4$-haloalkoxy; in particular hydroxyl, phenylthio or $NR^{12}R^{13}$;

$R^5$, $R^6$, $R^9$, $R^{10}$ independently of one another are hydrogen or $C_1$–$C_4$-alkyl, such as methyl or ethyl;

$R^7$ $R^8$ are hydrogen or $C_1$–$C_4$-alkyl, such as methyl or ethyl, or $R^7$ and $R^8$ together with the carbon atom to which they are attached form a carbonyl group;

$R^{12}$ is $C_1$–$C_4$-alkoxy, in particular methoxy or ethoxy;

$R^{13}$ is $C_1$–$C_4$-alkyl, in particular methyl or ethyl;

or $R^{12}$ and $R^{13}$ together with the nitrogen to which they are attached form a 5- or 6-membered unsaturated heterocycle which may have one or two further heteroatoms selected from the group consisting of O, N and S and which may be partially or fully halogenated and/or may carry one, two or three of the following radicals:

cyano, $C_1$–$C_4$-alkyl, $C_1$–$C_4$-haloalkyl, $C_1$–$C_4$-alkoxy or $C_1$–$C_4$-haloalkoxy;
in particular pyrrol-1-yl, pyrazol-1-yl, imidazol-1-yl, 1,2,3-triazol-1-yl, 1,2,4-triazol-1-yl or 1,3,4-triazol-1-yl;
especially pyrrol-1-yl or pyrazol-1-yl.

Variable n is preferably 2.

Emphasis is to be given to the following embodiments of the benzoylcyclohexenone derivatives of the formula I:

1. In a preferred embodiment of the benzoylcyclohexenones of the formula I:
   $R^1$ is $C_1$–$C_4$-alkyl or $C_1$–$C_4$-haloalkyl;
   in particular $C_1$–$C_4$-alkyl such as methyl, ethyl or n-propyl and especially methyl.
2. In a further preferred embodiment of the benzoylcyclohexenone derivatives of the formula I, n is 2 and $R^2$ is $C_1$–$C_4$-alkyl, especially methyl, ethyl or propyl, in particular methyl or ethyl.
3. In a further preferred embodiment of the benzoylcyclohexenone derivatives of the formula I:
   $R^3$ is halogen, such as fluorine, chlorine or bromine, cyano, nitro, $C_1$–$C_4$-alkoxy, $C_1$–$C_4$-haloalkoxy or $C_1$–$C_4$-alkylsulfonyl;
   in particular chlorine, cyano, nitro, $C_1$–$C_4$-alkoxy, $C_1$–$C_4$-haloalkoxy or $C_1$–$C_4$-alkylsulfonyl;
   particularly preferably $C_1$–$C_4$-alkoxy, $C_1$–$C_4$-haloalkoxy, $C_1$–$C_4$-alkylsulfonyl and very particularly preferably methoxy, difluoromethoxy, methylsulfonyl or ethylsulfonyl;
   and also halogen, such as fluorine, chlorine or bromine, cyano, nitro or $C_1$–$C_4$-alkylsulfonyl;
   in particular chlorine, cyano, nitro or $C_1$–$C_4$-alkylsulfonyl;
   particularly preferably $C_1$–$C_4$-alkylsulfonyl and very particularly preferably methylsulfonyl or ethylsulfonyl;
   and also $C_1$–$C_4$-alkoxy, such as methoxy or ethoxy, or $C_1$–$C_4$-haloalkoxy;
   in particular $C_1$–$C_4$-haloalkoxy, such as difluoromethoxy or trifluoromethoxy;
   and very particularly preferably difluoromethoxy.
4. In a further preferred embodiment of the benzoylcyclohexenone derivatives
   $R^4$ is hydroxyl.
5. In a further preferred embodiment of the benzoylcyclohexenone derivatives
   $R^4$ is phenylthio, where the phenyl ring may be partially or fully halogenated and/or may carry one to three of the follow radicals: nitro, cyano, $C_1$–$C_4$-alkyl, $C_1$–$C_4$-haloalkyl, $C_1$–$C_4$-alkoxy or $C_1$–$C_4$-haloalkoxy.
6. In a further preferred embodiment of the benzoylcyclohexenone derivatives
   $R^4$ is N-methoxy-N-methylamino, N-ethoxy-N-methylamino, N-methoxy-N-ethylamino, N-ethoxy-N-ethylamino, pyrrol-1-yl, pyrazol-1-yl, imidazol-1-yl, 1,2,3-triazol-1-yl, 1,2,4-triazol-1-yl or 1,3,4-triazol-1-yl, where the six last-mentioned radicals may be partially or fully halogenated and/or may carry one, two or three of the following radicals:
   cyano, $C_1$–$C_4$-alkyl, $C_1$–$C_4$-haloalkyl, $C_1$–$C_4$-alkoxy or $C_1$–$C_4$-haloalkoxy.
7. In a further preferred embodiment of the benzoylcyclohexenone derivatives
   $R^5$, $R^6$, $R^9$, $R^{10}$ are hydrogen or methyl;
   $R^7$, $R^8$ are hydrogen or methyl;
   or $R^7$ and $R^8$ together with the carbon atom to which they are attached form a carbonyl group;
   particularly preferably hydrogen or methyl.

Very particular preference is given to the compounds of the formula I in which
$R^1$ has the meanings given above and is in particular $C_1$–$C_4$-alkyl, especially methyl;
$R^2$ is $C_1$–$C_4$-alkyl or $C_1$–$C_4$-haloalkyl, in particular $C_1$–$C_4$-alkyl, especially methyl;
$R^3$ is $C_1$–$C_4$-alkylsulfonyl or $C_1$–$C_4$-haloalkylsulfonyl, in particular $C_1$–$C_4$-alkylsulfonyl, especially methylsulfonyl;
$R^4$ is hydroxyl;
$R^5$ to $R^{10}$ are hydrogen or methyl;
n is 2.

Very particular preference is also given to the compounds of the formula I in which
$R^1$ is $C_1$–$C_4$-alkyl;
$R^2$ is $C_1$–$C_4$-alkyl, in particular methyl, ethyl or propyl, especially methyl;
$R^3$ is halogen, such as chlorine, $C_1$–$C_4$-alkoxy, such as methoxy, $C_1$–$C_4$-haloalkoxy, such as difluoromethoxy, or $C_1$–$C_4$-alkylsulfonyl, such as methylsulfonyl, in particular $C_1$–$C_4$-alkoxy, such as methoxy, $C_1$–$C_4$-haloalkoxy, such as difluoromethoxy, or $C_1$–$C_4$-alkylsulfonyl, such as methylsulfonyl, especially $C_1$–$C_4$-haloalkoxy, such as difluoromethoxy, or $C_1$–$C_4$-alkylsulfonyl, such as methylsulfonyl;
$R^4$ is hydroxyl, phenylthio, where the phenyl radical may be partially or fully halogenated and/or may carry one to three of the following groups: nitro, cyano, $C_1$–$C_4$-alkyl, $C_1$–$C_4$-haloalkyl, $C_1$–$C_4$-alkoxy or $C_1$–$C_4$-haloalkoxy; N-methoxy-N-methylamino or 1-pyrazolyl;
in particular hydroxyl;
$R^5$ to $R^{10}$ are hydrogen or methyl;
n is 2.

Extreme preference is given to the compounds of the formula Ia (=I where $R^4$=hydroxyl and $R^5$ to $R^{10}$=hydrogen), in particular to the compounds Ia.1 to Ia.48 of Table 1, where the radical definitions $R^1$ to $R^{10}$ and n have a particular meaning for the compounds according to the invention, not only in combination with one another, but in each case also on their own.

TABLE 1

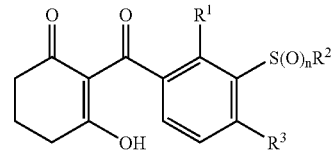

Ia

| No. | $R^1$ | $R^2$ | $R^3$ | n |
|---|---|---|---|---|
| Ia.1 | $CH_3$ | $CH_3$ | F | 2 |
| Ia.2 | $CH_3$ | $CH_3$ | Cl | 2 |
| Ia.3 | $CH_3$ | $CH_3$ | CN | 2 |
| Ia.4 | $CH_3$ | $CH_3$ | $NO_2$ | 2 |
| Ia.5 | $CH_3$ | $CH_3$ | $OCH_3$ | 2 |
| Ia.6 | $CH_3$ | $CH_3$ | $OCHF_2$ | 2 |
| Ia.7 | $CH_3$ | $CH_3$ | $SO_2CH_3$ | 2 |
| Ia.8 | $CH_3$ | $CH_3$ | $SO_2C_2H_5$ | 2 |
| Ia.9 | $CH_3$ | $C_2H_5$ | F | 2 |
| Ia.10 | $CH_3$ | $C_2H_5$ | Cl | 2 |
| Ia.11 | $CH_3$ | $C_2H_5$ | CN | 2 |
| Ia.12 | $CH_3$ | $C_2H_5$ | $NO_2$ | 2 |
| Ia.13 | $CH_3$ | $C_2H_5$ | $OCHF_2$ | 2 |
| Ia.14 | $CH_3$ | $C_2H_5$ | $OCH_3$ | 2 |

TABLE 1-continued

Ia

| No. | R¹ | R² | R³ | n |
|---|---|---|---|---|
| Ia.15 | $CH_3$ | $C_2H_5$ | $SO_2CH_3$ | 2 |
| Ia.16 | $CH_3$ | $C_2H_5$ | $SO_2C_2H_5$ | 2 |
| Ia.17 | $C_2H_5$ | $CH_3$ | F | 2 |
| Ia.18 | $C_2H_5$ | $CH_3$ | Cl | 2 |
| Ia.19 | $C_2H_5$ | $CH_3$ | CN | 2 |
| Ia.20 | $C_2H_5$ | $CH_3$ | $OCHF_2$ | 2 |
| Ia.21 | $C_2H_5$ | $CH_3$ | $NO_2$ | 2 |
| Ia.22 | $C_2H_5$ | $CH_3$ | $OCH_3$ | 2 |
| Ia.23 | $C_2H_5$ | $CH_3$ | $SO_2CH_3$ | 2 |
| Ia.24 | $C_2H_5$ | $CH_3$ | $SO_2C_2H_5$ | 2 |
| Ia.25 | $C_2H_5$ | $C_2H_5$ | F | 2 |
| Ia.26 | $C_2H_5$ | $C_2H_5$ | Cl | 2 |
| Ia.27 | $C_2H_5$ | $C_2H_5$ | $OCHF_2$ | 2 |
| Ia.28 | $C_2H_5$ | $C_2H_5$ | CN | 2 |
| Ia.29 | $C_2H_5$ | $C_2H_5$ | $NO_2$ | 2 |
| Ia.30 | $C_2H_5$ | $C_2H_5$ | $OCH_3$ | 2 |
| Ia.31 | $C_2H_5$ | $C_2H_5$ | $SO_2CH_3$ | 2 |
| Ia.32 | $C_2H_5$ | $C_2H_5$ | $SO_2C_2H_5$ | 2 |
| Ia.33 | $n-C_3H_7$ | $CH_3$ | F | 2 |
| Ia.34 | $n-C_3H_7$ | $CH_3$ | $OCHF_2$ | 2 |
| Ia.35 | $n-C_3H_7$ | $CH_3$ | Cl | 2 |
| Ia.36 | $n-C_3H_7$ | $CH_3$ | CN | 2 |
| Ia.37 | $n-C_3H_7$ | $CH_3$ | $NO_2$ | 2 |
| Ia.38 | $n-C_3H_7$ | $CH_3$ | $OCH_3$ | 2 |
| Ia.39 | $n-C_3H_7$ | $CH_3$ | $SO_2CH_3$ | 2 |
| Ia.40 | $n-C_3H_7$ | $CH_3$ | $SO_2C_2H_5$ | 2 |
| Ia.41 | $n-C_3H_7$ | $C_2H_5$ | $OCHF_2$ | 2 |
| Ia.42 | $n-C_3H_7$ | $C_2H_5$ | F | 2 |
| Ia.43 | $n-C_3H_7$ | $C_2H_5$ | Cl | 2 |
| Ia.44 | $n-C_3H_7$ | $C_2H_5$ | CN | 2 |
| Ia.45 | $n-C_3H_7$ | $C_2H_5$ | $NO_2$ | 2 |
| Ia.46 | $n-C_3H_7$ | $C_2H_5$ | $OCH_3$ | 2 |
| Ia.47 | $n-C_3H_7$ | $C_2H_5$ | $SO_2CH_3$ | 2 |
| Ia.48 | $n-C_3H_7$ | $C_2H_5$ | $SO_2C_2H_5$ | 2 |

Extreme preference is also given to the compounds of the formula Ib, in particular to the compounds Ib.1 to Ib.48 which differ from the compounds Ia.1 to Ia.48 in that $R^7$ is methyl.

Ib

Extreme preference is also given to the compounds of the formula Ic, in particular to the compounds Ic.1 to Ic.48 which differ from the compounds Ia.1 to Ia.48 in that $R^7$ and $R^8$ are methyl.

Ic

Extreme preference is also given to the compounds of the formula Id, in particular to the compounds Id.1 to Id.48 which differ from the compounds Ia.1 to Ia.48 in that $R^9$ and $R^{10}$ are methyl.

Id

Extreme preference is also given to the compounds of the formula Ie, in particular to the compounds Ie.1 to Ie.48 which differ from the compounds Ia.1 to Ia.48 in that $R^5$, $R^6$, $R^9$ and $R^{10}$ are methyl and $R^7$ and $R^8$ together with the carbon atom to which they are attached form a carbonyl group.

Ie

Extreme preference is also given to the compounds of the formula If, in particular to the compounds If.1 to If.48 which differ from the compounds Ia.1 to Ia.48 in that $R^4$ is phenylthio.

If

Extreme preference is also given to the compounds of the formula Ig, in particular to the compounds Ig.1 to Ig.48 which differ from the compounds Ia.1 to Ia.48 in that $R^4$ is phenylthio and $R^7$ is methyl.

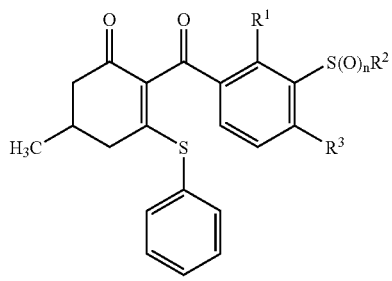

Ig

Extreme preference is also given to the compounds of the formula Ih, in particular to the compounds Ih.1 to Ih.48 which differ from the compounds Ia.1 to Ia.48 in that $R^4$ is phenylthio and $R^7$ and $R^8$ are methyl.

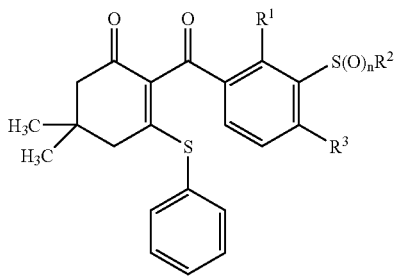

Ih

Extreme preference is also given to the compounds of the formula Ii, in particular to the compounds Ii.1 to Ii.48 which differ from the compounds Ia.1 to Ia.48 in that $R^4$ is phenylthio and $R^9$ and $R^{10}$ are methyl.

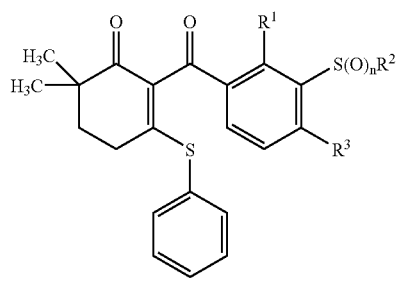

Ii

Extreme preference is also given to the compounds of the formula Ik, in particular to the compounds Ik.1 to Ik.48 which differ from the compounds Ia.1 to Ia.48 in that $R^4$ is phenylthio, $R^5$, $R^6$, $R^9$ and $R^{10}$ are methyl and $R^7$ and $R^8$ together with the carbon to which they are attached form a carbonyl group.

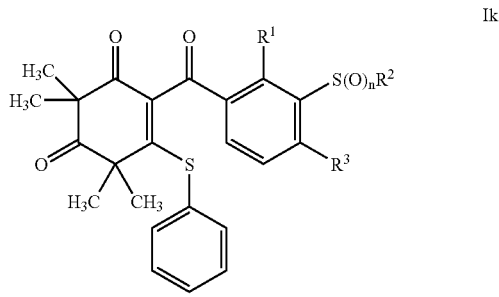

Ik

The compounds of the formula I can be prepared by many different routes.

A. The compound of the formula I in which $R^4$ is hydroxyl and $R^1$, $R^2$, $R^3$, $R^5$ to $R^{10}$ and n have the meanings given above are generally prepared by reacting an activated carboxylic acid IVb or a carboxylic acid IVa, which is preferably activated in situ, with a cyclohexane-1,3-dione of the formula III to give the acylation product, followed by rearrangement.

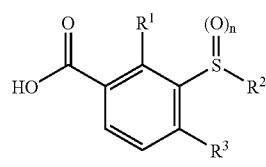

IVa

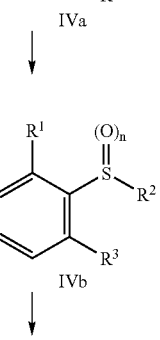

IVb

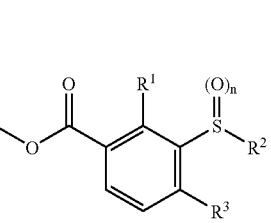

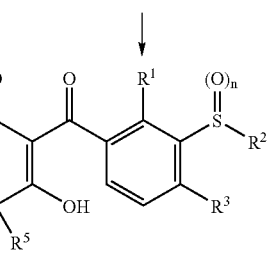

I (where $R^4$ = OH)

$L^1$ is a nucleophilically displaceable leaving group, such as halogen, for example bromine or chlorine, hetaryl, for example imidazolyl or pyridyl, carboxylate, for example acetate or trifluoroacetate, or the like.

The activated carboxylic acid IVb can be employed directly, as in the case of the carbonyl halides, or be generated in situ, using, for example, carbodiimides such as ethyl-(3'-dimethylaminopropyl)carbodiimide, dicyclohexylcarbodiimide, triphenylphosphine/azodicarboxylic ester, 2-pyridine disulfide/triphenylphosphine, carbonyldiimidazole or the like.

If appropriate, it may be advantageous to carry out the acylation reaction in the presence of a base. Here, starting materials and auxiliary base are expediently employed in equimolar amounts. In some cases, it may be advantageous to employ a slight excess of the auxiliary base, for example from 1.2 to 1.5 molar equivalents, based on IVa or IVb.

Suitable auxiliary bases are tertiary alkylamines, pyridine or alkali metal carbonates. Suitable solvents are, for example, chlorinated hydrocarbons, such as methylene chloride or 1,2-dichloroethane, aromatic hydrocarbons, such as toluene, xylene or chlorobenzene, ethers, such as diethyl ether, methyl tert-butyl ether, tetrahydrofuran or dioxane, organic nitriles, such as acetonitrile, amides, such as dimethylformamide, or dimethyl sulfoxide, or esters, such as ethyl acetate, or mixtures of these.

If the activated carboxylic acid component used is a halide, it may be expedient to cool the reaction mixture to 0–10° C. when adding this reactant. The mixture is subsequently stirred at 20–100° C., preferably at 25–50° C., until the reaction has gone to completion. Work-up is carried out in a customary manner, for example by pouring the reaction mixture into water and extracting the product of value. Solvents which are suitable for this purpose are, in particular, methylene chloride, diethyl ether and ethyl acetate. After the organic phase has been dried and the solvent has been removed, the crude ester can be employed for the rearrangement without further purification.

The rearrangement of the esters to give the compounds of formula I is expediently carried out at 20–100° C. in a solvent and in the presence of a base and, if appropriate, using a cyano compound as catalyst.

Suitable solvents are, for example, acetonitrile, methylene chloride, 1,2-dichloroethane, dioxane, ethyl acetate, toluene or mixtures of these. Preferred solvents are acetonitrile and dioxane.

Suitable bases are tertiary amines, such as triethylamine, aromatic amines, such as pyridine, or alkali metal carbonates, such as sodium carbonate or potassium carbonate, which are preferably employed in an equimolar amount or an up to four-fold excess, based on the ester. Preference is given to using triethylamine or alkali metal carbonate, preferably in twice the equimolar amount, based on the ester.

Suitable cyano compounds are inorganic cyanides, such as sodium cyanide or potassium cyanide, and organic cyano compounds, such as acetone cyanohydrin or trimethylsilyl cyanide. They are employed in an amount of 1–50 mol %, based on the ester. Preference is given to using acetone cyanohydrin or trimethylsilyl cyanide, for example in an amount of 5–15, preferably about 10, mol %, based on the ester.

Work-up can be carried out in a manner known per se. The reaction mixture is, for example, acidified with dilute mineral acid, such as 5% strength hydrochloric acid or sulfuric acid, and extracted with an organic solvent, for example methylene chloride or ethyl acetate. The organic extract can be extracted with 5–10% strength alkali metal carbonate solution, for example sodium carbonate or potassium carbonate solution. The aqueous phase is acidified and the precipitate that has formed is filtered off with suction and/or extracted with methylene chloride or ethyl acetate, dried and concentrated.

It is also possible to carry out the acylation reaction and the rearrangement reaction in a "one-pot process". To this end, the ester is prepared as described above and a catalyst and the base are then added to the reaction solution which contains the ester, and the rearrangement reaction is carried out as described above.

For this "one-pot process", it may also be suitable to add the base required for the two reactions at the beginning.

B. Compounds of the formula I where $R^4 = SR^{11}$ or $NR^{12}R^{13}$ in which $R^1$, $R^2$, $R^3$, $R^5$ to $R^{10}$ and n have the meanings given above can be obtained by reacting benzoylhalocyclohexenones of the formula V (Hal is halogen) with compounds of the formula $HSR^{11}$ or $HNR^{12}R^{13}$, if appropriate in the presence of a base or with prior salt formation.

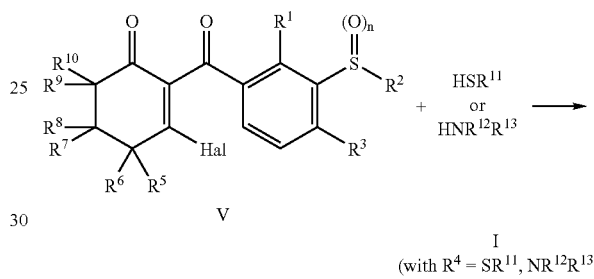

C. The preparation of compounds of the formula V in which $R^1$, $R^2$, $R^3$, $R^5$ to $R^{10}$ and n have the meanings given above is carried out, for example, by reacting benzoylcyclohexenone derivatives of the formula I (where $R^4$ =hydroxyl) with halogenating agents:

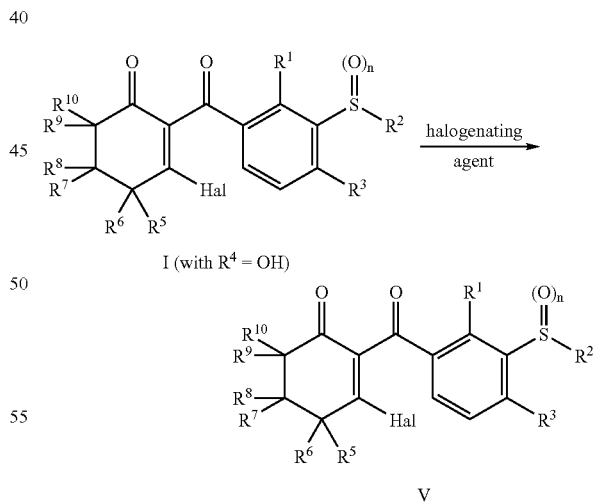

Suitable halogenating agents are, for example, phosgene, diphosgene, triphosgene, thionyl chloride, oxalyl chloride, phosphorus oxychloride, phosphorus pentachloride, mesyl chloride, chloromethylene-N,N-dimethylammonium chloride, oxalyl bromide, phosphorus oxybromide, etc.

For the reactions mentioned under points B and C, the following conditions apply:

The starting materials are generally employed in an equimolar ratio. However, it may also be advantageous to employ an excess of one or the other component.

If appropriate, it may be advantageous to carry out the reactions in the presence of a base. Here, the reactants and the base are expediently employed in equimolar amounts.

With a view to process B, it may in some cases be advantageous to use an excess of base, for example from 1.5 to 3 molar equivalents, in each case based on the starting material.

Suitable bases are tertiary alkylamines, such as triethylamine, aromatic amines, such as pyridine, alkali metal carbonates, for example sodium carbonate or potassium carbonate, alkali metal bicarbonates, such as sodium bicarbonate and potassium bicarbonate, alkali metal alkoxides, such as sodium methoxide, sodium ethoxide or potassium tert-butoxide, or alkali metal hydrides, for example sodium hydride. Preference is given to using triethylamine or pyridine.

Suitable solvents are, for example, chlorinated hydrocarbons, such as methylene chloride or 1,2-dichloroethane, aromatic hydrocarbons, for example toluene, xylene or chlorobenzene, ethers, such as diethyl ether, methyl tert-butyl ether, tetrahydrofuran or dioxane, polar aprotic solvents, such as acetonitrile, dimethylformamide or dimethyl sulfoxide, or esters, such as ethyl acetate, or mixtures of these.

The reaction temperature is generally in the range from 0° C. to the boiling point of the reaction mixture.

Work-up can be carried out in a manner known per se to afford the product.

The cyclohexanediones of the formula III used as starting materials are known or can be prepared by processes known per se (for example EP-A 71 707, EP-A 142 741, EP-A 243 313, U.S. Pat. No. 4,249,937, WO 92/13821).

The compounds of the formula IVb where $L^1$=halogen can be prepared similarly to methods known from the literature (cf. L. G. Fieser, M. Fieser "Reagents for Organic Synthesis", Vol. I, pp. 767–769 (1967)) by reacting the carboxylic acid of the formula IVa with halogenating agents such as thionyl chloride, thionyl bromide, phosgene, diphosgene, triphosgene, oxalyl chloride, oxalyl bromide, etc.

The compounds $HSR^{11}$ and $HNR^{12}R^{13}$ are likewise known or can be prepared by known processes.

The compound of the formula IVa can be prepared, for example, from commercially available nitroanilines of the formula VI.

D. Preparation of the compounds of the formula IVa where n=2

D.1 Compound IVa where n=2 and $R^3$ is alkylsulfonyl or haloalkylsulfonyl

Compounds IVa having this substitution pattern can be prepared, for example, according to scheme 1.

Scheme 1:

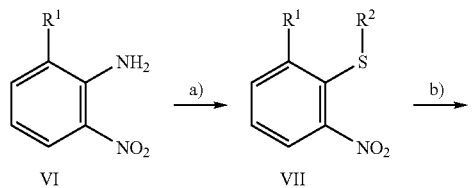

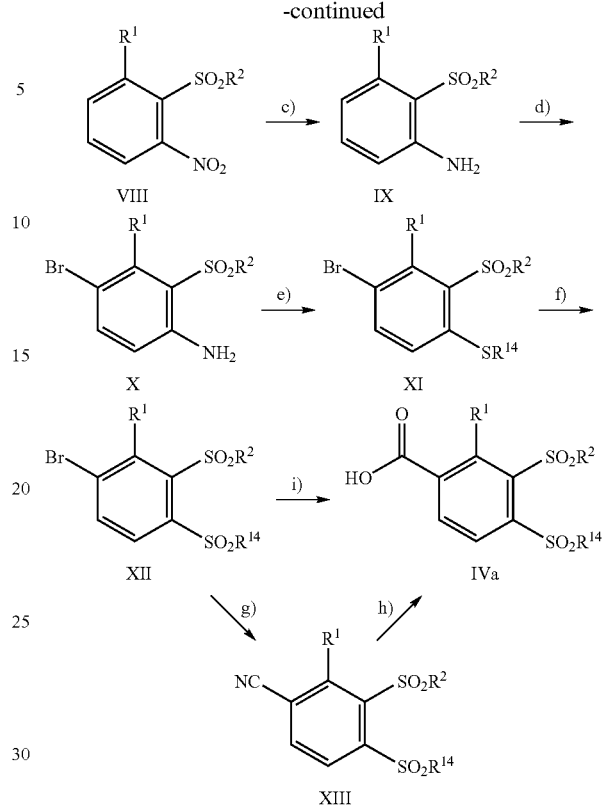

In scheme 1, $R^{14}$ is $C_1$–$C_6$-alkyl or $C_1$–$C_6$-haloalkyl ($SO_2R^{14}$ 5 $R^3$ for $C_1$–$C_6$-alkylsulfonyl or $C_1$–$C_6$-haloalkylsulfonyl), and $R^1$ and $R^2$ are as defined above.

According to scheme 1, in step a), the amino group in compound VI is initially converted into a thioalkyl group. To this end, the compound VI is reacted with a nitrite (such as, for example, an organic nitrite (R—ONO), for example n-butyl nitrite, isoamyl nitrite or tert-butyl nitrite, or an inorganic nitrite (for example sodium nitrite or potassium nitrite) in the presence of a mineral acid such as, for example, hydrochloric acid, sulfuric acid or phosphoric acid) in the presence of a dialkyl disulfide $R^2SSR^2$, such as dimethyl disulfide, diethyl disulfide, etc., where $R^2$ is as defined above, and in the presence of a catalyst.

The reaction of the compounds of the formula VI is generally carried out using from 1 to 3 equivalents of nitrite, preferably from 1 to 1.5 equivalents of nitrite. The nitrite used is preferably an alkyl nitrite. The reaction can be carried out in the presence of solvents. It is possible, for example, to use halogenated alkanes, such as 1,2-dichloroethane or methylene chloride, or aromatic compounds, such as benzene, toluene, chlorobenzene or nitrobenzene. If the reaction is carried out in a solvent, 1–3 equivalents of dialkyl disulfide, preferably 1–2 equivalents of dialkyl disulfide, are used. However, it is also possible to use the dialkyl disulfide as solvent. In a preferred embodiment, an excess of dialkyl disulfide is used as solvent, which is subsequently recovered by distillation.

Suitable for use as catalysts are transition metals or transition metal salts, such as, for example, copper powder, elemental copper in a different form, such as, for example, turnings, wire, granules, shot, rods; copper(I) salts, such as, for example, copper(I) chloride, copper(I) bromide or copper(I) iodide; copper(II) salts or elemental iodine; particularly preferably copper powder.

The temperature for the reaction is generally 40–150° C., preferably 50–100° C., particularly preferably 60–90° C. For a further reaction, the product may be used without further purification. If desired, the product may also be purified, for example by distillation, crystallization, etc.

A further route to the alkylthio or haloalkylthio compound is to convert the compound of the formula VI in a manner known per se via diazotization into the corresponding diazonium salt and to convert the latter with hydrogen sulfide, an alkali metal sulfide or a xantogenate into the corresponding mercapto compound. The resulting mercapto compound is then converted in a thioether synthesis by reaction with alkyl halides $R^2$-Hal into the alkylthio or haloalkylthio group, for example by reaction with methyl halide into the methylthio group or by reaction with chloro- or bromodichloromethane into the difluoromethylthio group. Suitable solvents are inert organic solvents, for example hydrocarbons such as toluene or hexane, ethers such as diethyl ether, dimethoxyethane, methyl tert-butyl ether, dioxane or tetrahydrofuran or alcohols such as methanol or ethanol.

The thioether VII can be converted by treatment with one equivalent of oxidizing agent into the corresponding sulfinyl (halo)alkyl compound (step b)). On addition of a further equivalent of oxidizing agent, the sulfinyl(halo)alkyl compound affords the corresponding sulfonyl(halo)alkyl compound VIII. Suitable oxidizing agents are, for example, tert-butyl hydroperoxide, organic peracids such as m-chloroperbenzoic acid, peracetic acid or trifluoroperacetic acid, hydrogen peroxide, if appropriate in the presence of a catalyst, such as tungstate.

The thio(halo)alkyl compounds are preferably converted directly into the sulfonyl(halo)alkyl compounds VIII by using two equivalents of oxidizing agent, if appropriate in the presence of a catalyst, such as tungstate.

Suitable solvents are organic solvents which are inert to oxidation, such as, for example, chlorinated hydrocarbons, such as methylene chloride, chloroform, carbon tetrachloride or 1,2-dichloroethane, aromatic hydrocarbons, for example toluene, xylene or chlorobenzene, cyclic or acyclic alkanes, such as cyclohexane, hexane, pentane, heptane and petroleum ether, ethers, such as diethyl ether, methyl tert-butyl ether, tetrahydrofuran and dioxane, organic nitriles, such as acetonitrile, amides, such as dimethylformamide, or mixtures of these. If the oxidation is carried out using an organic peracid, the solvent used is preferably the parent organic acid, i.e., for example, formic, acetic or trifluoroacetic acid, if appropriate in a mixture with one or more of the abovementioned solvents.

The reaction temperature is usually in the range between the melting point and the boiling point of the reaction mixture, preferably in the range from 0° C. to 150° C.

In step c), the nitro group of the compound VIII is then reduced to the amino group, giving the sulfonylated aniline IX. Suitable reducing agents are, for example, hydrazines, metal hydrides, such as aluminum hydride, and complex hydrides derived therfrom, such as lithium aluminum hydride or diisobutylaluminum hydride, or boranes, and also nascent hydrogen, for example iron, zinc or tin in the presence of acids, such as hydrochloric acid or carboxylic acids, such as acetic acid. A further suitable reducing agent is hydrogen in the presence of catalytic amounts of transition metals such as nickel, palladium, platinum, ruthenium or rhodium. The transition metals can be used as such or in supported form, for example on activated carbon, in the form of activated metals, for example Raney nickel, or in the form of soluble complex compounds. The reaction is preferably carried out in a solvent. Suitable solvents for the reduction are, depending on the solubility of the substrate to be hydrogenated and the chosen reducing agent, for example $C_1$–$C_4$-alcohols, such as methanol, ethanol, n-propanol, isopropanol or n-butanol, halogenated $C_1$–$C_6$ hydrocarbons, such as dichloromethane, trichloromethane, trichloroethane, trichloroethylene, aromatic hydrocarbons, such as benzene, toluene, xylenes, chlorobenzene, carboxylates, such as ethyl acetate, aqueous solutions of inorganic acids, such as aqueous hydrochloric acid, or organic acids, and mixtures thereof with water. The reduction is usually carried out at temperatures in the range from −15° C. to +100° C., preferably in the range from 0° C. to 60° C. The reduction with hydrogen is usually carried out at a hydrogen pressure in the range from 1 to 50 bar. Catalytic hydrogenations with hydrogen are preferably carried out in the range from 1 to 10 bar. For the catalytic hydrogenation of aromatic nitro groups, see, for example, Rylander in "Catalytic Hydrogenation over Platinum Metals", Academic Press, New York, 1967, 168–202; Furst et al., Chem. Rev. 65 (1965), 52; Tepko et al., J. Org. Chem. 45 (1980), 4992.

Bromination of the sulfonylated aniline IX in step d) leads to the 4-bromoaniline X. Brominating agents suitable for this purpose are customary brominating agents such as bromine, etc., preferably oligobromine compounds, such as pyridinium tribromide, dioxane dibromide or quaternary ammonium polybromides, such as tetrabutylammonium tribromide.

In general, the reaction is carried out in the presence of a base, such as alkali metal carbonate or alkaline earth metal carbonate, for example sodium carbonate, potassium carbonate, magnesium carbonate or calcium carbonate, or alkali metal bicarbonate, for example sodium bicarbonate. Preference is given to using an at least stoichiometric amount of base, in particular a 1.5- to 5-fold excess, based on IX.

Suitable solvents are inert organic solvents, such as, for example, aliphatic or cycloaliphatic hydrocarbons, for example n-hexane or cyclohexane, halogenated hydrocarbons, for example dichloromethane, trichloromethane, carbon tetrachloride, trichloroethane, trichloroethylene, heteroaromatic compounds, such as pyridine, polar aprotic solvents, such as acetonitrile, or anhydrous inorganic or organic acids, such as acetic acid.

The reaction temperature is usually between the melting point of the reaction mixture and 60° C., preferably in the range from 0° C. to 40° C.

If the brominating agent used is bromine or a mixture of hydrobromic acid and hydrogen peroxide, the reaction is preferably carried out in the solvent pyridine or in a solvent mixture comprising at least 80% by weight of pyridine. Additional solvents suitable for solvent mixtures are, for example, methanol, ethyl acetate, butyl acetate, water, etc.

The aniline IX is initially charged as a solution or suspension in pyridine or in a pyridine-containing solvent mixture. The brominating agent is then added over a period of from 1 minute to 5 hours, depending on the scale of the reaction. The addition is carried out either directly, i.e. in the absence of a solvent, or together with a solvent.

If the brominating agent used is bromine, the addition is preferably carried out together with a suitable solvent, such as, for example, pyridine with formation of pyridinium bromide. In this case, the selectivity in the ratio of monobromo to dibromo compounds is particularly high.

In a preferred embodiment, brominating agent and aniline IX are employed in a molar ratio of from 1:1 to 2:1. The brominating agent is preferably employed in an equimolar amount or in a slight excess.

The reaction is usually carried out at temperatures from 20° C. to the boiling point of the solvent, preferably in the range from 60 to 85° C.

The reaction time is from 1 to 24 hours, preferably from 2 to 12 hours, in particular from 5 to 8 hours.

The conversion of the amino group of the 4-bromoaniline X into an alkylthio or haloalkylthio group in step e) can be achieved, for example, in the manner described above in step a). This gives the bromothioether XI.

In step f), the bromothioether XI is then subjected to an oxidation similarly to step b), giving the bromobenzene XII.

The bromobenzene XII is subsequently converted into the carboxylic acid IVa. To this end, XII can initially be converted into the nitrile XIII (step g)), and this can then be hydrolyzed to give the carboxylic acid IVa (step h)).

The nitrile XIII can be prepared, for example, by reacting XII with copper(I) cyanide in a Rosenmund-von-Braun reaction (cf., for example, Org. Synth. Vol. III (1955), 212). The reaction is usually carried out at elevated temperature in the range above 100° C., preferably in the range from 120 to 180° C. A suitable solvent is dimethylformamide, for example.

Step i) in scheme 1 can also be realized by reacting the bromo compound XII with carbon monoxide, a base and water, under elevated pressure in the presence of a palladium, nickel, cobalt or rhodium catalyst.

Nickel, cobalt, rhodium and in particular palladium can be employed in metallic form or in the form of customary salts, such as in the form of halogen compounds, for example palladium(II) chloride, rhodium(III) chloride hydrate, acetates, for example palladium(II) acetate, cyanides, etc., in the known valence states. Metal complexes with tertiary phosphines, metal alkyl carbonyls, metal carbonyls, for example $CO_2(CO)_8$, $Ni(CO)_4$, metal carbonyl complexes with tertiary phosphines, for example $(PPh_3)_2Ni(CO)_2$, or transition metal salts complexed with tertiary phosphines can also be employed. The last-mentioned embodiment is preferred, in particular when the catalyst used is palladium. Here, the type of phosphine ligand is of minor important. Suitable ligands are, for example, those of the formulae:

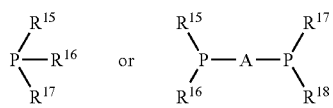

where the radicals $R^{15}$ to $R^{18}$ are low-molecular-weight alkyl, for example $C_1$–$C_6$-alkyl, cycloalkyl, such as cyclohexyl, aryl, $C_1$–$C_4$-alkylaryl, for example benzyl or phenethyl, or aryloxy. Aryl is, for example, naphthyl, anthryl and preferably unsubstituted or substituted phenyl, where, with respect to the substituents, attention has to be paid only to their inertness to the carboxylation reaction, otherwise they can be varied widely and include all inert organocarbon radicals, such as $C_1$–$C_6$-alkyl radicals, for example methyl, carboxyl radicals, such as COOH, COOM (M is, for example, an alkali metal, alkaline earth metal or ammonium salt), or organocarbon radicals attached via oxygen, such as $C_1$–$C_6$-alkoxy radicals. A is a divalent organic radical, for example $C_1$–$C_4$-alkylene, 1,2-cycloalkylene, α,α'-ferrocenediyl, α,α-biphenyl or similar bifunctional groups.

The phosphine complexes can be prepared in a manner known per se. For example, customary commercially available metal salts such as palladium(II) chloride or palladium (II) acetate are used as starting materials, and the phosphine, for example $P(C_6H_5)_3$, $P(n-C_4H_9)_3$, $PCH_3(C_6H_5)_2$, 1,2-bis (diphenylphosphino)ethane, tricyclohexylphosphine, is added.

The amount of phosphine, based on the transition metal, is usually from 0 to 20, in particular from 0.1 to 10, molar equivalents, particularly preferably from 1 to 5 molar equivalents.

The amount of transition metal is not critical. Of course, for reasons of cost, preference is given to using a small amount, for example from 0.1 to 10 mol %, in particular from 1 to 5 mol %, based on the starting material IVa.

For preparing the carboxylic acid IVa, the reaction is carried out with carbon monoxide and at least equimolar amounts of water, based on the bromine compound XII. The reaction component water can simultaneously also serve as solvent, i.e. the maximum amount is not critical.

However, depending on the nature of the starting materials and the catalysts used, it may also be advantageous for the solvent used to be, instead of the reaction component, another inert solvent or the base which is used for the carboxylation.

Suitable inert solvents for carboxylation reactions are customary solvents such as hydrocarbons, for example toluene, xylene, hexane, pentane, cyclohexane, ethers, for example methyl tert-butyl ether, tetrahydrofuran, dioxane, dimethoxyethane, substituted amides, such as dimethylformamide, persubstituted ureas, such as tetra-$C_1$–$C_4$-alkylureas, or nitriles, such as benzonitrile or acetonitrile.

In a preferred embodiment of the process, one of the reaction components, in particular the base, is used in excess, so that no additional solvent is necessary.

Bases which are suitable for the process are all inert bases which are able to bind hydrogen iodide or hydrogen bromide liberated during the reaction. Examples which may be mentioned here are tertiary amines, such as tert-alkylamines, for example trialkylamines such as triethylamine, cyclic amines, such as N-methylpiperidine or N,N'-dimethylpiperidine, pyridine, alkali metal carbonates or alkali metal bicarbonates, or tetraalkyl-substituted urea derivatives, such as tetra-$C_1$–$C_4$-alkylurea, for example tetramethylurea.

The amount of base is not critical. Customarily from 1 to 10, in particular from 1 to 5, mol are used. When the base is simultaneously used as solvent, the amount is generally such that the reaction components are dissolved, unnecessarily high excesses being avoided for reasons of practicability in order to save costs, to be able to employ small reaction vessels and to ensure that the reaction components have maximum contact.

During the reaction, the carbon monoxide pressure is adjusted such that an excess of CO, based on the bromide, is always present. At room temperature, the carbon monoxide pressure is prefer-ably from 1 to 250 bar, in particular from 5 to 150 bar, of CO.

The carbonylation is generally carried out continuously or batch-wise at temperatures of from 20° C. to 250° C., in particular from 30° C. to 150° C. In the case of batchwise operation, carbon monoxide is advantageously continuously injected onto the reaction mixture to maintain a constant pressure.

D.2 Compound IVa where n=2 and $R^3$ is halogen, cyano, nitro, $C_1$–$C_6$-alkyl, $C_1$–$C_6$-haloalkyl, $C_1$–$C_6$-alkoxy, $C_1$–$C_6$-haloalkoxy, $C_1$–$C_6$-alkylsulfinyl or $C_1$–$C_6$-haloalkylsulfinyl.

The preparation of compounds IVa having this substitution pattern is shown in scheme 2.

reaction with chloro- or bromodifluoromethane into the difluoromethoxy group. The reaction is preferably carried out in the presence of a strong base. Examples of suitable bases are alkali metal hydroxides such as sodium hydroxide or potassium hydroxide, alkali metal carbonates such as potassium carbonate or sodium

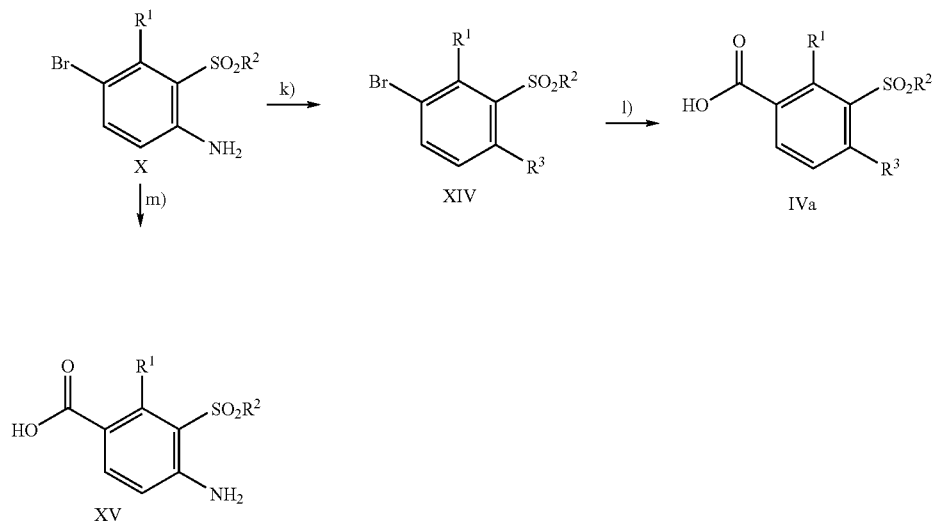

Scheme 2:

In scheme 2, $R^1$ and $R^2$ are as defined above.

The conversion can be carried out, for example, by converting the amino group in X with a nitrosating agent "NO$^+$" into a diazonium group, analogously to processes known from the literature. The resulting diazonium group is subsequently reacted in a customary manner, it being possible to generate the radicals $R^3$ listed below:

$R^3$=cyano or halogen {for example by a Sandmeyer reaction: cf., for example, Houben-Weyl, Methoden der Organischen Chemie [[Methods of Organic Chemistry], Georg Thieme Verlag Stuttgart, Vol. 5/4, 4th Edition 1960, p. 438 ff.};

$R^3$=alkyl or haloalkyl by reaction with alkenes or haloalkenes in a Meerwein arylation, cf., for example, C. S. Rondestredt, Org. React. 11 (1960), 189, and H. P. Doyle et al., J. Org. Chem. 42 (1977), 2431};

$R^3$=nitro {for example by Sandmeyer reaction: cf. E. Profft, Chemiker Ztg. 74 (1950), 455; or by oxidation: cf. Angew. Chem. 113 (2001), 419 ff.);

$R^3$=alkoxy or haloalkoxy: conversion of the diazonium group into a hydroxyl group {for example by heating the diazonium salt to give a phenol: cf., for example, Org. Synth. Coll. Vol. 3 (1955), 130}. The hydroxyl group is then, in an ether synthesis, converted into an alkoxy or haloalkoxy group by reaction with alkyl halides, for example by reaction with methyl halide such as methyl iodide into the methoxy group or by carbonate, or alkali metal bicarbonates, such as sodium bicarbonate, or organic bases, for example alkoxides such as sodium methoxide or ethoxide or potassium methoxide or ethoxide, in particular tertiary amines, such as triethylamine or pyridine;

$R^3$=$C_1$–$C_6$-alkylsulfinyl or haloalkylsulfinyl {cf. scheme 1, step a)}. Conversion of the diazonium group into the alkylthio or haloalkylthio group, followed by selective oxidation to give the (halo)alkylsulfinyl group, cf., for example, step b) in scheme 1, where only one equivalent of oxidizing agent is used for the oxidation.

Suitable nitrosating agents are: nitrosonium tetrafluoroborate, nitrosyl chloride, nitrosylsulfuric acid, the abovementioned alkyl nitrides or salts of nitrous acids, such as, for example, sodium nitride.

In the compound XIV where $R^3$=halogen or in the acid IVa where $R^3$=halogen, $R^3$ can be converted into a cyano group, for example by reaction with copper(I) cyanide similarly to T. Naito et al., Chem. Pharm. Bull. 16 (1968), 148–159.

E. Preparation of the compounds of the formula IVa where n=0 or 1

E.1 Compounds IVa where n=0 or 1 and $R^3$ is $C_1$–$C_6$-alkylthio or $C_1$–$C_6$-haloalkylthio The preparation of compounds IVa having this substitution pattern is shown in scheme 3.

Scheme 3:

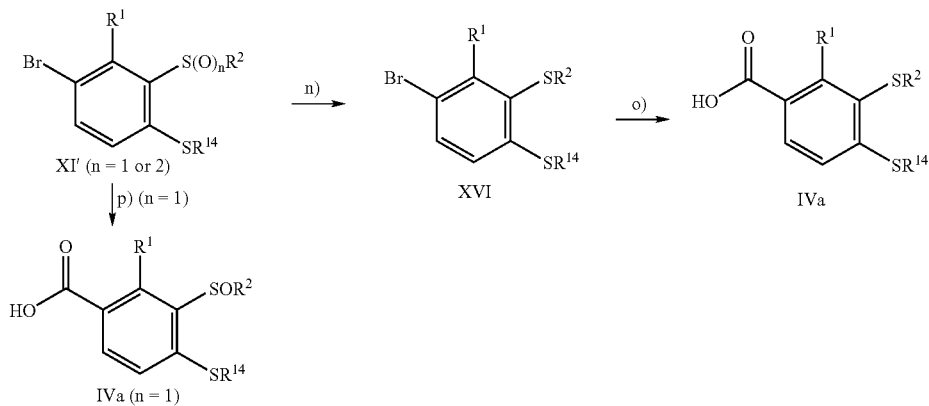

In scheme 3, $R^{14}$ is $C_1$–$C_6$-alkyl or $C_1$–$C_6$-haloalkyl, and $R^1$ and $R^2$ are as defined above.

According to scheme 3, starting with compound VI, the compound XI' where n is 1 or 2 is initially prepared, analogously to scheme 1. Subsequent reduction of the compound XI' in step n) gives the compound XVI. Suitable reducing agents for the sulfoxide XI' (n is 1) are, for example, metal hydrides such as lithium aluminum hydride, tributyltin hydride, $CH_3SiCl_3$—NaI, $PCl_3$, acetyl chloride, triphenylphosphine, tris(dimethylamino)phosphine-$I_2$. A further suitable reducing agent is hydrogen in the presence of catalytic amounts of transition metals such as palladium. The transition metals are, if appropriate, present in supported form, for example on activated carbon. Agents suitable for reducing the sulfone XI' (n is 2) are, for example, complex metal hydrides, such as diisobutylaluminum hydride. Alternatively, the sulfones XI' (n is 2) can also be reduced to the sulfides XVI by heating with sulfur. XVI is then converted into the acid IVa (n is 0) according to the process illustrated in scheme 1.

The acid IVa where n is 1 can be prepared, for example, from sulfoxide XI' (n=1), analogously to the process illustrated in scheme 1.

It is also possible to prepare the sulfide XVI from the thioether VII. Analogously to step c) in scheme 1, the nitro group is converted into an amino group. After subsequent bromination—analogously to step d) in scheme 1—the $SR^{14}$ radical is introduced-analogously to step e) in scheme 1.

E.2 Compounds IVa where n=0 or 1 and $R^3$ is halogen, cyano, nitro, $C_1$–$C_6$-alkyl, $C_1$–$C_6$-haloalkyl, $C_1$–$C_6$-alkoxy, $C_1$–$C_6$-haloalkoxy.

The preparation of compounds IVa having this substitution pattern is shown in scheme 4.

Scheme 4:

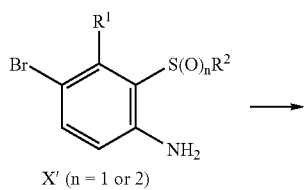

-continued

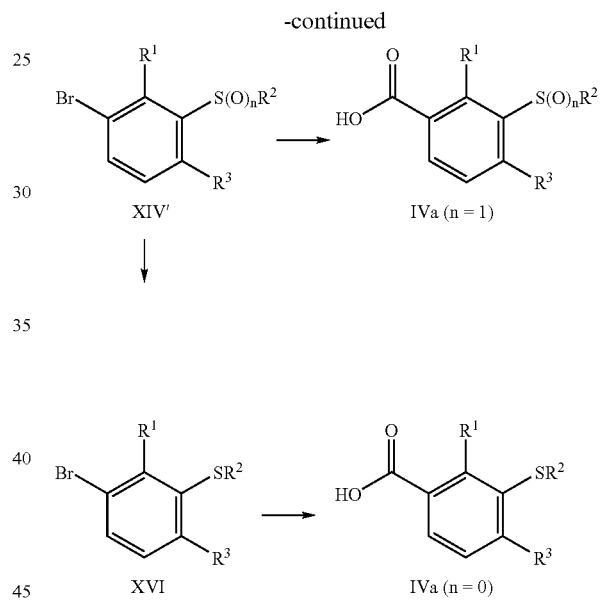

In scheme 4, $R^1$ and $R^2$ are as defined above.

Conversion of the amino group in X' into a halogen, cyano, nitro, $C_1$–$C_6$-alkyl, $C_1$–$C_6$-haloalkyl, $C_1$–$C_6$-alkoxy or $C_1$–$C_6$-haloalkoxy group with formation of the compound XIV' can be carried out, for example, analogously to scheme 2. The reduction of the sulfoxide XIV' (n=1) or the sulfone XIV' (n=2) to the sulfide XVI and subsequent conversion into the carboxylic acid IVa (n=0) is carried out according to the process illustrated in scheme 3.

The acid IVa (n is 1) can be prepared, for example, from sulfoxide XIV' (n=1), analogously to the process illustrated in scheme 1.

A further route to the compounds XIV' (n is 1 or 2) and the compounds XVI in which $R^1$ and $R^2$ are as defined above and $R^3$ is $C_1$–$C_6$-alkyl, $C_1$–$C_6$-haloalkyl, $C_1$–$C_6$-alkoxy, $C_1$–$C_6$-haloalkoxy or halogen is shown in scheme 5.

Scheme 5:

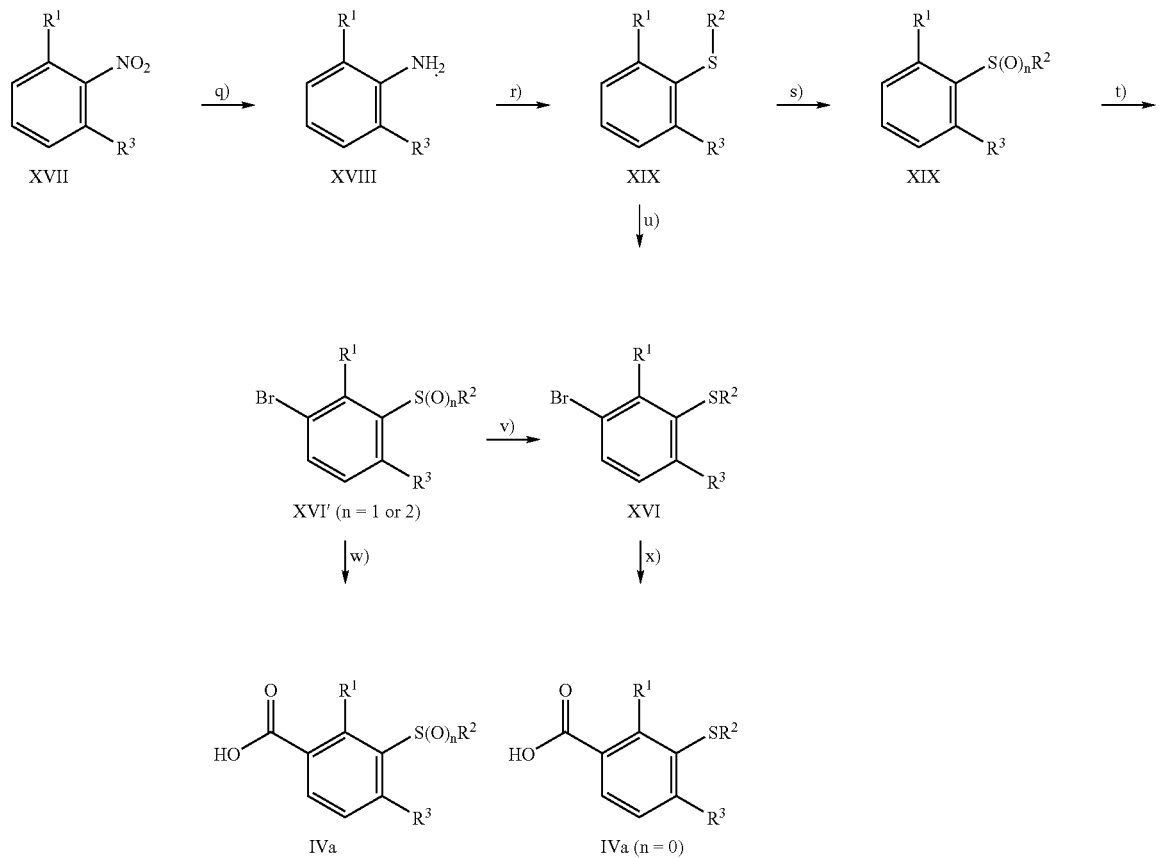

In scheme 5, $R^1$ and $R^2$ are as defined above.

According to scheme 5, it is possible to prepare, starting with nitrobenzenes XVII and analogously to the reactions described in scheme 1, the compounds XIV' and XVI, which can then be converted into the corresponding acids IVa.

It is also possible to convert the compound XIX as described above (scheme 1, step d) into the bromine compound XVI. Furthermore, the acid IVa in which $R^3$ is $NO_2$ and n is 0, 1 or 2 can be prepared, for example, according to scheme 6.

Scheme 6:

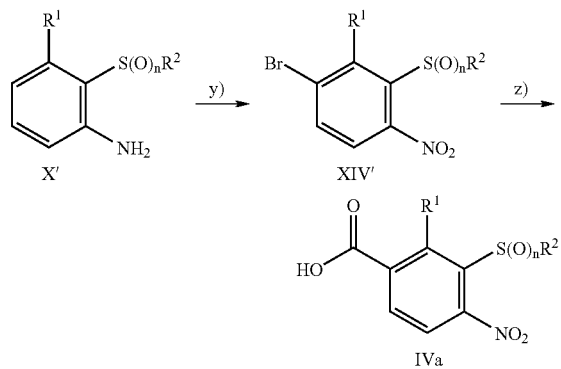

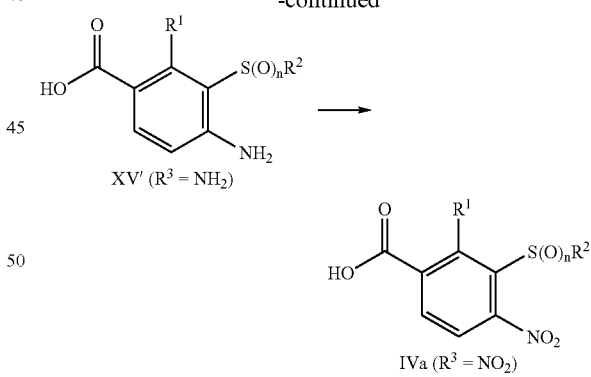

In scheme 6, $R^1$ is as defined above and n is 0, 1 or 2.

Amino compounds of the formula X' or of the formula IVa where $R^3=NH_2$, for example, can be converted by oxidation into the corresponding nitro compounds XIV' and IVa, respectively. Such conversions are described, for example, in Angew. Chem. 113 (2001), 419 ff. The compounds XIV' are then converted into the carboxylic acid IVa, analogously to the reactions described in scheme 1.

The further procedure for converting XIV' into the carboxylic acid IVa corresponds to the processes described above.

If appropriate, it may be advantageous to rearrange the order of the reaction steps described above in schemes 1, 2, 3, 4, 5 and 6, or else to combine the reaction steps with one another.

Work-up of the reaction mixtures obtained is generally carried out by known procedures, for example by crystallization, aqueous-extractive work-up, by chromatographic methods or by combinations of these methods.

The examples below serve to illustrate the invention:

2-[2-Methyl-3,4-di(methylsulfonyl)benzoyl]cyclohexane-1,3-dione (Compound Ia.7)

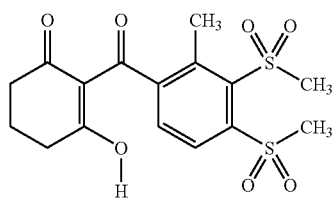

1.1 2-Methyl-6-nitrothioanisole 160 g of copper powder and 500 ml of dimethyl disulfide were added to 357 g (3.12 mol) of tert-butyl nitrite. At 50–52° C., a solution of 316 g (2.08 mol) of 2-methyl-6-nitroaniline in 1600 ml of dimethyl disulfide was added dropwise, and the mixture was stirred at 50–55° C. for 4 hours. After cooling, the reaction mixture was filtered off with suction through kieselguhr, and dichloromethane was added to the filtrate. The organic phase was washed with dilute hydrochloric acid and then with water and subsequently dried over magnesium sulfate. Concentration under high vacuum gave 452 g of 2-methyl-6-nitrothioanisole as a red-black oil which was used for the next reaction step without further purification.

1.2 3-Methyl-2-methylsulfonylnitrobenzene

With ice-cooling, 383 g (3.4 mol) of 30% strength hydrogen peroxide were added dropwise over a period of 45 min to a solution of 207 g (1.13 mol) of 2-methyl-6-nitrothioanisole and 11.2 g of sodium tungstate hydrate in 1.5 l of anhydrous acetic acid. The reaction mixture was stirred at room temperature for 16 hours, and a further 192 g (1.7 mol) of 30% strength hydrogen peroxide were then added dropwise. The reaction mixture was then introduced into 2 kg of ice-water and stirred for another 30 min. The white residue was filtered off with suction and washed three times with water. After 16 hours of drying under reduced pressure at 30° C., 158 g of 3-methyl-2-methylsulfonylnitrobenzene were obtained, in a yield of 65%, calculated for the two steps.

1.3 3-Methyl-2-methylsulfonylaniline

A solution of 158 g (0.74 mol) of 3-methyl-2-methylsulfonylnitrobenzene in 1.5 l of ethyl acetate and 5 g of a catalyst comprising 10% by weight of palladium on carbon were introduced into a hydrogenation apparatus fitted with gas inlet tube. The hydrogenation apparatus was flushed twice with nitrogen. Hydrogen was then introduced, and the mixture was stirred at 45° C. for 48 hours. The reaction mixture was filtered off with suction through kieselguhr and the filtrate was concentrated under reduced pressure, giving 134 g (98% of theory) of 3-methyl-2-methylsulfonylaniline as an orange-yellow solid.

1.4 4-Bromo-3-methyl-2-methylsulfonylaniline 400 g (2.9 mol) of potassium carbonate were added to a solution of 134 g (0.73 mol) of 3-methyl-2-methylsulfonylaniline in 1200 ml of acetonitrile. At room temperature, 320 g (0.65 mol) of tetrabutylammonium tribromide were then added a little at a time, with vigorous stirring. The resulting precipitate was separated off, methyl tert-butyl ether was added to the filtrate and the filtrate was extracted with dilute hydrochloric acid and then with water. The organic phase was concentrated to dryness under reduced pressure. The resulting residue was once more taken up in methyl tert-butyl ether and washed two more times with hydrochloric acid and water. The organic phase was dried and concentrated under reduced pressure, giving 142 g (74%) of 4-bromo-3-methyl-2-methylsulfonylaniline as a brown solid of melting point 103–106° C.

1.5 4-Bromo-3-methyl-2-methylsulfonylthioanisole 75 g of copper powder and 100 ml of dimethyl disulfide were added to 92 g (0.8 mol) of tert-butyl nitrite. At 50–52° C., a solution of 142 g (0.54 mol) of 4-bromo-3-methyl-2-methylsulfonyl aniline in 600 ml of dimethyl disulfide was added dropwise, and the mixture was stirred at 50–55° C. for 7 hours. After cooling, the mixture was filtered off with suction through kieselguhr, and dichloromethane was added to the filtrate. The organic phase was washed with dilute hydrochloric acid and then with water. After drying over sodium sulfate, the organic phase was concentrated under high vacuum. This gave 170 g of the title compound as a black oil which was used for the next reaction step without further purification.

1.6 2-Methyl-3,4-di(methylsulfonyl)bromobenzene

With ice-cooling, 195 g (1.7 mol) of 30% strength hydrogen peroxide were added dropwise over a period of 45 min to a solution of 170 g (0.58 mol) of 4-bromo-3-methyl-2-methylsulfonylthioanisole and 5.7 g of sodium tungstate hydrate in 1 l of anhydrous acetic acid. The reaction mixture was stirred at room temperature for 16 hours. A further 98 g (0.86 mol) of 30% strength hydrogen peroxide were then added dropwise. The reaction mixture was stirred into 4 kg of ice-water and stirred for 30 min. The resulting white residue was filtered off with suction and washed three times with water. After 16 hours of drying under reduced pressure at 30° C., 181 g of crude 2-methyl-3,4-di(methylsulfonyl) bromobenzene of melting point 169–171° C. were obtained.

1.7 2-Methyl-3,4-di(methylsulfonyl)benzoic acid 1.5 l of toluene, 750 ml of water, 83 g (0.25 mol) of 2-methyl-3,4-di(methylsulfonyl)bromobenzene, 51 g (0.15 mol) of triethylamine, 11 g (0.25 mol) of lithium chloride, 3.56 g (0.013 mol) of tricyclohexylphosphine and 1.44 g (6.4 mmol) of palladium acetate were initially charged in a 3.5 l autoclave. The autoclave was then flushed twice with nitrogen, and a carbon monoxide pressure of 10 bar was applied. With vigorous stirring using a gas-dispersion stirrer, the reaction mixture was heated to 140° C. The carbon monoxide pressure was increased to 15 bar, and the mixture was stirred at 140° C. for 24 h. During the reaction, the pressure was maintained by applying additional carbon monoxide. The autoclave was then cooled and vented. The reaction discharge was filtered off with suction through a depth filter, and the phases were separated. The toluene phase was washed with triethylamine/water. The combined aqueous phases were adjusted to pH 1 using 18% strength hydrochloric acid and extracted with ethyl acetate. The organic phase was dried over sodium sulfate and the solvent was removed, giving 40 g (55% yield) of 2-methyl-3,4-di(methylsulfonyl)benzoic acid as a beige solid of melting point 192–198° C.

1.8 2-Methyl-3,4-di(methylsulfonyl)benzoyl chloride

A few drops of dimethylformamide were added to a solution of 63 g (0.22 mol) of 2-methyl-3,4-di(methylsulfonyl)benzoic acid in 550 ml of toluene, and 36 g (0.3 mol) of thionyl chloride were then added dropwise. The reaction mixture was heated at reflux for 1.5 hours. After cooling, the reaction mixture was concentrated. This gave 62 g (93% yield) of 2-methyl-3,4-di(methylsulfonyl)benzoyl chloride as a beige solid.

1.9 2-[2-Methyl-3,4-di(methylsulfonyl)benzoyl]cyclohexane-1,3-dione 61 g (0.6 mol) of triethylamine were added to a suspension of 23 g (0.2 mol) of cyclohexane-1,3-dione in 100 ml of acetonitrile, and a solution of 62 g (0.2 mol) of the acid chloride from 1.8 in 500 ml of acetonitrile was then added dropwise with stirring at 0–10° C. The reaction mixture was subsequently stirred at this temperature for another hour, allowed to warm to room temperature and treated with 1 g of trimethylsilyl cyanide. After 12 hours of stirring at room temperature, the reaction mixture was concentrated and the residue was taken up in dichloromethane and extracted with dilute hydrochloric acid and then twice with water. The organic phase was then extracted with 5% strength potassium carbonate solution. The aqueous phase was then adjusted to pH 5–6 using 10% strength hydrochloric acid and extracted with dichloromethane. The organic phase was dried and the solvent removed, giving 66 g (86% yield) of the title compound as a beige solid of melting point 301–302° C.

In addition to the above compound, Tables 2 to 4 list further derivatives of the formula I which were prepared in an analogous manner.

TABLE 2

| Compound | $R^3$ | $R^5$ | $R^6$ | $R^7$ | $R^8$ | $R^9$ | $R^{10}$ | Physical data m.p. [° C.] |
|---|---|---|---|---|---|---|---|---|
| 2.1 | $SO_2CH_3$ | H | H | H | H | H | H | 301–302 |
| 2.2 | $SO_2CH_3$ | $CH_3$ | $CH_3$ | =O | | $CH_3$ | $CH_3$ | 237–240 |
| 2.3 | $SO_2CH_3$ | H | H | $CH_3$ | H | H | H | 235–239 |
| 2.4 | $SO_2CH_3$ | H | H | H | H | $CH_3$ | $CH_3$ | oil |
| 2.5 | $SO_2CH_3$ | H | H | $CH_3$ | $CH_3$ | H | H | oil |
| 2.6 | Cl | H | H | H | H | H | H | 137–140 |
| 2.7 | $OCH_3$ | H | H | H | H | H | H | 121–129 |
| 2.8 | $OCH_3$ | H | H | $CH_3$ | $CH_3$ | H | H | 163–165 |
| 2.9 | $OCH_3$ | H | H | $CH_3$ | H | H | H | 106–112 |
| 2.10 | $OCHF_2$ | H | H | H | H | H | H | 64–69 |
| 2.11 | $OCHF_2$ | H | H | $CH_3$ | $CH_3$ | H | H | oil |
| 2.12 | $OCHF_2$ | H | H | $CH_3$ | H | H | H | oil |
| 2.13 | Cl | H | H | $CH_3$ | H | H | H | oil |
| 2.14 | Cl | H | H | $CH_3$ | $CH_3$ | H | H | oil |
| 2.15 | $OCH_3$ | $CH_3$ | $CH_3$ | =O | | $CH_3$ | $CH_3$ | oil |
| 2.16 | $OCHF_2$ | $CH_3$ | $CH_3$ | =O | | $CH_3$ | $CH_3$ | oil |
| 2.17 | Cl | $CH_3$ | $CH_3$ | =O | | $CH_3$ | $CH_3$ | oil |

TABLE 3

| No. | $R^3$ | $R^4$ | $R^5$ | $R^6$ | $R^7$ | $R^8$ | $R^9$ | $R^{10}$ | Physical data m.p. [° C.] |
|---|---|---|---|---|---|---|---|---|---|
| 3.1 | $SO_2CH_3$ | 1-pyrazolyl | H | H | H | H | H | H | 275–277 |
| 3.2 | $SO_2CH_3$ | 1-pyrazolyl | H | H | $CH_3$ | H | H | H | 278–283 |
| 3.3 | $SO_2CH_3$ | $S(C_6H_5)$ | H | H | H | H | H | H | 250–254 |
| 3.4 | $SO_2CH_3$ | $S(C_6H_5)$ | H | H | $CH_3$ | H | H | H | 252–255 |
| 3.5 | $SO_2CH_3$ | $NCH_3(OCH_3)$ | H | H | H | H | H | H | 183–186 |
| 3.6 | $SO_2CH_3$ | $NCH_3(OCH_3)$ | H | H | $CH_3$ | H | H | H | 108–110 |
| 3.7 | $OCH_3$ | $S(C_6H_5)$ | H | H | $CH_3$ | $CH_3$ | H | H | 122–125 |
| 3.8 | $OCHF_3$ | $S(C_6H_5)$ | H | H | H | H | H | H | oil |

TABLE 4

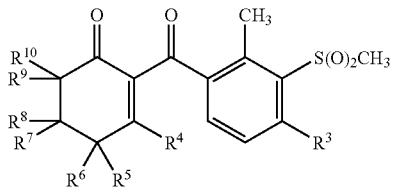

| No. | $R^2$ | $R^3$ | $R^5$ | $R^6$ | $R^7$ | $R^8$ | $R^9$ | $R^{10}$ | Physical data m.p. [° C.] |
|---|---|---|---|---|---|---|---|---|---|
| 4.1 | $(CH_2)_2CH_3$ | $SO_2CH_3$ | H | H | H | H | H | H | 182–184 |

The compounds I and their agriculturally useful salts are suitable, both in the form of isomer mixtures and in the form of the pure isomers, as herbicides. The herbicidal compositions comprising compounds of the formula I control vegetation on non-crop areas very efficiently, especially at high rates of application. They act against broad-leaved weeds and harmful grasses in crops such as wheat, rice, corn, soybean and cotton without causing any significant damage to the crop plants. This effect is mainly observed at low rates of application.

Depending on the application method used, the compounds I or the compositions comprising them can additionally be employed in a further number of crop plants for eliminating undesirable plants. Examples of suitable crops are the following:

*Allium cepa, Ananas comosus, Arachis hypogaea, Asparagus officinalis, Beta vulgaris* spec. *altissima, Beta vulgaris* spec. *rapa, Brassica napus* var. *napus, Brassica napus* var. *napobrassica, Brassica rapa* var. *silvestris, Camellia sinensis, Carthamus tinctorius, Carya illinoinensis, Citrus limon, Citrus sinensis, Coffea arabica (Coffea canephora, Coffea liberica), Cucumis sativus, Cynodon dactylon, Daucus carota, Elaeis guineensis, Fragaria vesca, Glycine max, Gossypium hirsutum, (Gossypium arboreum, Gossypium herbaceum, Gossypium vitifolium), Helianthus annuus, Hevea brasiliensis, Hordeum vulgare, Humulus lupulus, Ipomoea batatas, Juglans regia, Lens culinaris, Linum usitatissimum, Lycopersicon lycopersicum, Malus* spec., *Manihot esculenta, Medicago sativa, Musa* spec., *Nicotiana tabacum (N.rustica), Olea europaea, Oryza sativa, Phaseolus lunatus, Phaseolus vulgaris, Picea abies, Pinus* spec., *Pisum sativum, Prunus avium, Prunus persica, Pyrus communis, Ribes sylvestre, Ricinus communis, Saccharum officinarum, Secale cereale, Solanum tuberosum, Sorghum bicolor (s. vulgare), Theobroma cacao, Trifolium pratense, Triticum aestivum, Triticum durum, Vicia faba, Vitis vinifera* and *Zea mays.*

In addition, the compounds I may also be used in crops which tolerate the action of herbicides owing to breeding, including genetic engineering methods.

The compounds I, or the herbicidal compositions comprising them, can be used for example in the form of ready-to-spray aqueous solutions, powders, suspensions, also highly concentrated aqueous, oily or other suspensions or dispersions, emulsions, oil dispersions, pastes, dusts, materials for broadcasting or granules, by means of spraying, atomizing, dusting, broadcasting, watering or treatment of the seed or mixing with the seed. The use forms depend on the intended aims; in any case, they should ensure a very fine distribution of the active compounds according to the invention. The herbicidal compositions comprise a herbicidally effective amount of at least one compound of the formula I or an agriculturally useful salt of I and auxiliaries customarily used for formulating crop protection agents.

Essentially, suitable inert auxiliaries include: mineral oil fractions of medium to high boiling point, such as kerosene and diesel oil, furthermore coal tar oils and oils of vegetable or animal origin, aliphatic, cyclic and aromatic hydrocarbons, e.g. paraffins, tetrahydronaphthalene, alkylated naphthalenes and their derivatives, alkylated benzenes and their derivatives, alcohols such as methanol, ethanol, propanol, butanol and cyclohexanol, ketones such as cyclohexanone, strongly polar solvents, e.g. amines such as N-methylpyrrolidone, and water.

Aqueous use forms can be prepared from emulsion concentrates, suspensions, pastes, wettable powders or water-dispersible granules by adding water. To prepare emulsions, pastes or oil dispersions, the benzoylcyclohexenone derivatives of the formula I, either as such or dissolved in an oil or solvent, can be homogenized in water by means of a wetting agent, tackifier, dispersant or emulsifier. Alternatively, it is also possible to prepare concentrates consisting of active substance, wetting agent, tackifier, dispersant or emulsifier and, if desired, solvent or oil, which are suitable for dilution with water.

Suitable surfactants are the alkali metal salts, alkaline earth metal salts and ammonium salts of aromatic sulfonic acids, e.g. ligno-, phenol-, naphthalene- and dibutylnaphthalenesulfonic acid, and of fatty acids, alkyl- and alkylarylsulfonates, alkyl sulfates, lauryl ether sulfates and fatty alcohol sulfates, and salts of sulfated hexa-, hepta- and octadecanols, and also of fatty alcohol glycol ethers, condensates of sulfonated naphthalene and its derivatives with formaldehyde, condensates of naphthalene, or of the naphthalenesulfonic acids with phenol and formaldehyde, polyoxyethylene octylphenol ether, ethoxylated isooctyl-, octyl- or nonylphenol, alkylphenyl polyglycol ether or tributylphenyl polyglycol ether, alkylaryl polyether alcohols, isotridecyl alcohol, fatty alcohol ethylene oxide condensates, ethoxylated castor oil, polyoxyethylene alkyl ethers or polyoxypropylene alkyl ethers, lauryl alcohol polyglycol ether acetate, sorbitol esters, lignosulfite waste liquors or methylcellulose.

Powders, materials for broadcasting and dusts can be prepared by mixing or grinding the active substances together with a solid carrier.

Granules, e.g. coated granules, impregnated granules and homogeneous granules, can be prepared by binding the active compounds to solid carriers. Solid carriers are mineral earths, such as silicas, silica gels, silicates, talc, kaolin, limestone, lime, chalk, bole, loess, clay, dolomite, diatomaceous earth, calcium sulfate, magnesium sulfate, magnesium oxide, ground synthetic materials, fertilizers such as ammonium sulfate, ammonium phosphate, ammonium nitrate and ureas, and products of vegetable origin, such as cereal meal, tree bark meal, wood meal and nutshell meal, cellulose powders, or other solid carriers.

The concentrations of the active compounds I in the ready-to-use preparations can be varied within wide ranges. In general, the formulations comprise from about 0.001 to 98% by weight, preferably from 0.01 to 95% by weight of at least one active compound. The active compounds are employed in a purity of from 90% to 100%, preferably from 95% to 100% (according to the NMR spectrum).

The compounds I according to the invention can be prepared, for example, as follows:

I. 20 parts by weight of an active compound of the formula I are dissolved in a mixture consisting of 80 parts by weight of alkylated benzene, 10 parts by weight of the adduct of from 8 to 10 mol of ethylene oxide to 1 mol of oleic acid N-monoethanolamide, 5 parts by weight of calcium dodecylbenzenesulfonate and 5 parts by weight of the adduct of 40 mol of ethylene oxide to 1 mol of castor oil. Pouring the solution into 100,000 parts by weight of water and finely distributing it therein gives an aqueous dispersion which comprises 0.02% by weight of the active compound.

II. 20 parts by weight of an active compound of the formula I are dissolved in a mixture consisting of 40 parts by weight of cyclohexanone, 30 parts by weight of isobutanol, 20 parts by weight of the adduct of 7 mol of ethylene oxide to 1 mol of isooctylphenol and 10 parts by weight of the adduct of 40 mol of ethylene oxide to 1 mol of castor oil. Pouring the solution into 100,000 parts by weight of water and finely distributing it therein gives an aqueous dispersion which comprises 0.02% by weight of the active compound.

III. 20 parts by weight of an active compound of the formula I are dissolved in a mixture consisting of 25 parts by weight of cyclohexanone, 65 parts by weight of a mineral oil fraction of boiling point from 210 to 280° C. and 10 parts by weight of the adduct of 40 mol of ethylene oxide to 1 mol of castor oil. Pouring the solution into 100,000 parts by weight of water and finely distributing it therein gives an aqueous dispersion which comprises 0.02% by weight of the active compound.

IV. 20 parts by weight of an active compound of the formula I are mixed thoroughly with 3 parts by weight of sodium diisobutylnaphthalenesulfonate, 17 parts by weight of the sodium salt of a lignosulfonic acid from a sulfite waste liquor and 60 parts by weight of pulverulent silica gel, and the mixture is ground in a hammer mill. Finely distributing the mixture in 20,000 parts by weight of water gives a spray mixture which comprises 0.1% by weight of the active compound.

V. 3 parts by weight of an active compound of the formula I are mixed with 97 parts by weight of finely divided kaolin. This gives a dust which comprises 3% by weight of the active compound.

VI. 20 parts by weight of an active compound of the formula I are mixed intimately with 2 parts by weight of calcium dodecylbenzenesulfonate, 8 parts by weight of fatty alcohol polyglycol ether, 2 parts by weight of the sodium salt of a phenol/urea/formaldehyde condensate and 68 parts by weight of a paraffinic mineral oil. This gives a stable oily dispersion.

VII. 1 part by weight of an active compound of the formula I is dissolved in a mixture consisting of 70 parts by weight of cyclohexanone, 20 parts by weight of ethoxylated isooctylphenol and 10 parts by weight of ethoxylated castor oil. This gives a stable emulsion concentrate.

VIII. 1 part by weight of an active compound of the formula I is dissolved in a mixture of 80 parts by weight of cyclohexanone and 20 parts by weight of Wettol® EM 31 (nonionic emulsifier based on ethoxylated castor oil). This gives a stable emulsion concentrate.

The herbicidal compositions or the active compounds can be applied pre- or post-emergence or together with the seed of a crop plant. If the active compounds are less well tolerated by certain crop plants, application techniques may be used in which the herbicidal compositions are sprayed, with the aid of the spraying equipment, in such a way that they come into contact as little as possible, if at all, with the leaves of the sensitive crop plants, while the active compounds reach the leaves of undesirable plants growing underneath, or the bare soil surface (post-directed, lay-by).

The application rates of compound I are from 0.001 to 3.0, preferably from 0.01 to 1.0 kg/ha of active substance (a.s.), depending on the control target, the season, the target plants and the growth stage.

To widen the activity spectrum and to achieve synergistic effects, the compounds I may be mixed with a large number of representatives of other herbicidal or growth-regulating active compound groups and then applied concomitantly. Suitable components for mixtures are, for example, 1,2,4-thiadiazoles, 1,3,4-thiadiazoles, amides, aminophosphoric acid and its derivatives, aminotriazoles, anilides, (het)aryloxyalkanoic acids and their derivatives, benzoic acid and its derivatives, benzothiadiazinones, 2-aroyl-1,3-cyclohexanediones, 2-hetaroyl-1,3-cyclohexanediones, hetarylaryl ketones, benzylisoxazolidinones, meta-$CF_3$-phenyl derivatives, carbamates, quinolinecarboxylic acid and its derivatives, chloroacetanilides, cyclohexenone oxime ether derivatives, diazines, dichloropropionic acid and its derivatives, dihydrobenzofurans, dihydrofuran-3-ones, dinitroanilines, dinitrophenols, diphenyl ether, dipyridyls, halocarboxylic acids and their derivatives, ureas, 3-phenyluracils, imidazoles, imidazolinones, N-phenyl-3,4,5,6-tetrahydrophthalimides, oxadiazoles, oxiranes, phenols, aryloxy- and hetaryloxyphenoxypropionic esters, phenylacetic acid and its derivatives, phenylpropionic acid and its derivatives, pyrazoles, phenylpyrazoles, pyridazines, pyridinecarboxylic acid and its derivatives, pyrimidyl ethers, sulfonamides, sulfonylureas, triazines, triazinones, triazolinones, triazolecarboxamides and uracils.

It may furthermore be advantageous to apply the compounds I, alone or else concomitantly in combination with other herbicides, or in the form of a mixture with other crop protection agents, for example together with agents for controlling pests or phytopathogenic fungi or bacteria. Also of interest is the miscibility with mineral salt solutions, which are employed for treating nutritional and trace element deficiencies. Non-phytotoxic oils and oil concentrates may also be added.

USE EXAMPLES

The herbicidal activity of the benzoylcyclohexenones of the formula I was demonstrated by the following greenhouse experiments:

The cultivation containers used were plastic flower pots containing loamy sand with approximately 3.0% of humus as the substrate. The seeds of the test plants were sown separately for each species.

For the pre-emergence treatment, directly after sowing the active compounds, which had been suspended or emulsified in water, were applied by means of finely distributing nozzles. The containers were irrigated gently to promote germination and growth and subsequently covered with transparent plastic hoods until the plants had rooted.

This cover caused uniform germination of the test plants, unless this was adversely affected by the active compounds.

For the post-emergence treatment, the test plants were first grown to a height of from 3 to 15 cm, depending on the plant habit, and only then treated with the active compounds which had been suspended or emulsified in water. The test plants were for this purpose either sown directly and grown in the same containers, or they were first grown separately as seedlings and transplanted into the test containers a few days prior to treatment. The application rate for the post-emergence treatment was 0.125 and 0.0625 kg of a.s. (active substance)/ha.

Depending on the species, the plants were kept at 10–25° C. or 20–35° C. The test period extended over 2 to 4 weeks. During this time, the plants were tended, and their response to the individual treatments was evaluated.

The evaluation was carried out using a scale from 0 to 100. 100 means no emergence of the plants, or complete destruction of at least the aerial parts and 0 means no damage, or normal course of growth.

The plants used in the greenhouse experiments were of the following species:

| Bayer code | Common name |
|---|---|
| ABUTH | velvetleaf |
| AMARE | redroot pigweed |
| AVEFA | wild oats |
| BRAPL | alexander grass |
| CHEAL | lambsquarters |
| ECHCG | barnyard grass |
| PHBPU | morning glory |
| POLPE | ladys thumb |
| SETFA | giant foxtail |

At application rates of 0.125 or 0.0625 kg/ha, the compound No. 2.1 shows very good herbicidal post-emergence activity against ECHCG, ABUTH, CHEAL and POLPE.

At application rates of 0.125 or 0.0625 kg/ha, the compound No. 2.2 shows very good herbicidal post-emergence activity against AVEFA, ECHCG, CHEAL und POLPE.

At application rates of 0.125 or 0.0625 kg/ha, the compound No. 2.5 shows very good herbicidal post-emergence activity against ECHCG, SETFA, AMARE und CHEAL.

At application rates of 0.125 or 0.0625 kg/ha, the compound No. 2.4 shows very good herbicidal post-emergence activity against ECHCG, SETFA, PHBPU und CHEAL.

At application rates of 0.125 or 0.0625 kg/ha, the compound No. 2.3 shows very good herbicidal post-emergence activity against ECHCG, ABUTH, CHEAL und PHBPU.

At application rates of 0.125 or 0.0625 kg/ha, the compound No. 2.6 shows very good herbicidal post-emergence activity against ECHCG, SETFA, ABUTH und POLPE.

The invention claimed is:
1. A benzoylcyclohexenone derivative of the formula I

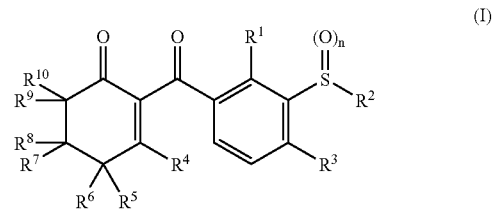

in which the variables are as defined below:
$R^1$ is $C_3$–$C_6$-alkyl, $C_3$–$C_6$-haloalkyl or $C_1$–$C_4$-alkoxy-$C_1$–$C_4$-alkyl;
$R^2$ is $C_1$–$C_6$-alkyl or $C_1$–$C_6$-haloalkyl;
$R^3$ is halogen, cyano, nitro, $C_1$–$C_6$-alkyl, $C_1$–$C_6$-haloalkyl, $C_1$–$C_6$-haloalkoxy, $C_1$–$C_6$haloalkylthio, $C_1$–$C_6$-alkylsulfinyl, $C_1$–$C_6$-haloalkylsulfinyl, $C_1$–$C_6$-alkylsul-fonyl or $C_1$–$C_6$-haloalkylsulfonyl;
$R^4$ is hydroxyl or $SR^{11}$;
$R^5$, $R^6$, $R^9$ $R^{10}$ independently of one another are hydrogen or $C_1$–$C_4$-alkyl;
$R^7$, $R^8$ independently of one another are hydrogen or $C_1$–$C_4$-alkyl or together with the carbon atom to which they are attached form a carbonyl group;
n is 1 or 2;
where
$R^{11}$ is $C_1$–$C_4$-alkyl or phenyl which is optionally partially or fully halogenated and/or optionally carries one to three of the following groups: nitro, cyano, $C_1$–$C_4$-alkyl, $C_1$–$C_4$-haloalkyl, $C_1$–$C_4$-alkoxy or $C_1$–$C_4$-haloalkoxy;
and its agriculturally useful salts.
2. A benzoylcyclohexenone derivative as claimed in claim 1 in which $R^1$ in formula I is $C_3$–$C_4$-alkyl.
3. A benzoylcyclohexenone derivative as claimed in claim 1 in which $R^2$ in formala I is $C_1$–$C_4$-alkyl or $C_1$–$C_4$-haloalkyl and n is 2.
4. A benzoylcyclohexenone derivative as claimed in claim 1 in which $R^3$ in formula I is selected from the group consisting of halogen, cyano, nitro, $C_1$–$C_4$-haloalkoxy, $C_1$–$C_4$-haloalkylthio, $C_1$–$C_4$-alkylsulfinyl, $C_1$–$C_4$-haloalkylsulfinyl, $C_1$–$C_4$-alkylsulfonyl, $C_1$–$C_4$-haloalkylsulfonyl.
5. A bensoylcyclohexenone derivative as claimed in claim 4 in which $R^3$ in formula I is halogen, cyano, nitro, $C_1$–$C_4$-haloalkoxy or $C_1$–$C_4$-alkylsulfonyl.
6. A benzoylcyclohexenone derivative as claimed in claim 5 in which $R^3$ in formula I is $C_1$–$C_4$-haloalkoxy.
7. A benzoylcyclohexenone derivative as claimed in claim 5 in which $R^3$ in formula I is $C_1$–$C_4$-alkylsulfonyl.
8. A benzoylcyclohexenone derivative as claimed in claim 1 in which $R^4$ in the formula I is $SR^{11}$.
9. 2-[2-Methyl-3,4-di(methylsulfonyl)benzoyl]cyclohexane-1,3-dione.
10. 5-Methyl-2-[2-methyl-3,4-di(methylsulfonyl)benzoyl]-cyclohexane-1,3-dione.
11. A composition which comprises a herbicidally effective amount of at least one benzoylcyclohexenotte derivative of the formula I or an agriculturally useful salt thereof as claimed in claim 1 and auxiliaries customary for formulating crop protection agents.
12. A method for controlling undesirable vegetation, which comprises allowing a herbicidally effective amount of at least one benzoylcyclohexenone derivative of the formula I or an agriculturally useful salt of I as claimed in claim 1 to act on plants, their habitat and/or on seed.

13. A benzoylcyclohexenone derivative of the formula I

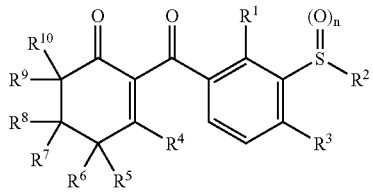

(I)

in which the variables are as defined below:
- $R_1$ is $C_1$–$C_6$-alkyl, $C_1$–$C_6$-haloalkyl or $C_1$–$C_4$-alkoxy-$C_1$–$C_4$-alkyl;
- $R^2$ is $C_1$–$C_6$-alkyl or $C_1$–$C_6$-haloalkyl;
- $R^3$ is halogen, cyano, nitro, $C_1$–$C_6$-alkyl, $C_1$–$C_6$-haloalkyl, $C_1$–$C_6$-haloalkoxy, $C_1$–$C_6$haloalkylthio, $C_1$–$C_6$-alkylsulfinyl, $C_1$–$C_6$-haloalkylsulfinyl, $C_1$–$C_6$-alkylsulfonyl or $C_1$–$C_6$-haloalkylsulfonyl;
- $R^4$ is hydroxyl;
- $R^5, R^6, R^9 R^{10}$ independently of one another are hydrogen or $C_1$–$C_4$-alkyl;
- $R^7, R^8$ independently of one another are hydrogen or $C_1$–$C_4$-alkyl or together with the carbon atom to which they are attached form a carbonyl group;
- n is 1 or 2;

and its agriculturally useful salts.

14. A benzoylcyclohexenone derivative as claimed in claim 13 in which $R^1$ in formula I is $C_1$–$C_4$-alkyl.

15. A benzolylcyclohexenone derivative as claimed in claim 13 in which $R^2$ in formula I is $C_1$–$C_4$-alkyl or $C_1$–$C_4$-haloalkyl and n is 2.

16. A benzolycyclohexenone derivative as claimed in claim 13 in which $R^3$ in formula I is selected from the group consisting of halogen, cyano, nitro, $C_1$–$C_4$-haloalkoxy, $C_1$–$C_4$-haloalkylthio, $C_1$–$C_4$-alkylsulfinyl, $C_1$–$C_4$-haloalkylsulfinyl, $C_1$–$C_4$-alkylsulfonyl, $C_1$–$C_4$-haloalkylsulfonyl.

17. A benzoylcyclohexenone derivative as claimed in claim 16 in which $R^3$ in formula I is halogen, cyano, nitro, $C_1$–$C_4$-haloalkoxy or $C_1$–$C_4$-alkylsulfonyl.

18. A benzoylcyclohexenone derivative as claimed in claim 17 in which $R^3$ in formula I is $C_1$–$C_4$-haloalkoxy or $C_1$–$C_4$-alkylsulfonyl.

19. A composition which comprises a herbicidally effective amount of at least one benzoylcyclohexenone derivative of the formula I or an agriculturally useful salt thereof as claimed in claim 13 and auxiliaries customary for formulating crop protection agents.

20. A method for controlling undesirable vegetation, which comprises allowing a herbicidally effective amount of at least one benzoylcyclohexenone derivative of the formula I or an agriculturally useful salt of I as claimed in claim 13 to act on plants, their habitat and/or on seed.

21. A benzoylcyclohexenone derivative as claimed in claim 13, selected from the group consisting of
- 2-[2-methyl-3,4-di (methylsulfonyl)benzoyl]cyclohexane-1,3-dione,
- 4,4-dimethyl-2-[2-methyl-3,4-di(methylsulfonyl)benzyl] cyolohex- an-1,3,5-trione,
- 5-methyl-2-[2-methyl-3,4-di(methylsulfonyl)benzoyl]cyclohex- ane-1,3-dione,
- 4,4-dimethyl-2-[2-methyl-3,4-di(methylsulfonyl)benzoyl]cyclohex- ane-1,3-dione,
- 5,5-dimethyl-2-[2-methyl-3,4-di(methylsulfonyl)benzoyl]cyclohex- ane-1,3-dione, and
- 2-[4-chloro-2-methyl-3-methylsulfonylbenzoyl]cyclohexane-1,3-di- one.

22. A benzolycyclohexenone derivative as claimed in claim 1 in which
- n is 2,
- $R^2$ is $C_1$–$C_4$-alkyl or $C_1$–$C_4$-haloalkyl, and
- $R^3$ is halogen, cyano, nitro, $C_1$–$C_4$-haloalkoxy, $C_1$–$C_4$-haloalkyl- thio, $C_1$–$C_4$-alkylsulfinly, $C_1$–$C_4$-haloalkylsul- finyl, $C_1$–$C_4$- alkylsulfonyl or $C_1$–$C_4$-haloalkylsulfonyl

23. A benzoylcyclohexenone derivative as claimed in claim 13 in which
- n is 2,
- $R^1$ is $C_1$–$C_4$-alkyl
- $R^2$ $C_1$–$C_4$-alkyl or $C_1$–$C_4$-haloalkyl; and
- $R^3$ is halogen, cyano, nitro, $C_1$–$C_4$-haloalkoxy, $C_1$–$C_4$-haloalkyl- thio, $C_1$–$C_4$-alkylsulfinyl, $C_1$–$C_4$-haloalkylsul- finyl, $C_1$–$C_4$- alkylsulfonyl or $C_1$–$C_4$-haloalkylsulfonyl.

24. A benzoylcyclohexenone derivative as claimed in claim 23 in which $R^3$ is halogen, cyano, nitro, $C_1$–$C_4$-haloalkoxy or $C_1$–$C_4$-alkylsulfonyl.

25. A benzoylcyclohexenone derivative as claimed in claim 24 in which $R^3$ in formula I is $C_1$–$C_4$-haloalkoxy or $C_1$–$C_4$-alkylsulfonyl.

* * * * *

UNITED STATES PATENT AND TRADEMARK OFFICE
CERTIFICATE OF CORRECTION

PATENT NO. : 7,196,229 B2
APPLICATION NO. : 10/485922
DATED : March 27, 2007
INVENTOR(S) : von Deyn et al.

It is certified that error appears in the above-identified patent and that said Letters Patent is hereby corrected as shown below:

In Claim 1, col. 38, indicated lines 21–22:
"$C_1$–$C_6$–alkylsul–fonyl" should read --$C_1$–$C_6$–alkylsulfonyl--
In Claim 11, col. 38, indicated line 22:
"benzoylcyclohexenotte" should read --benzoylcyclohexenone--
In Claim 21, col. 40, indicated lines 15–16:
"4,4–dimethyl–2–[2–methyl–3,4–di(methylsulfonyl)benzyl]cyclohex– an–1,3,5–trione,"
should read
--4,4--dimethyl–2–[2–methyl–3,4–di(methylsulfonyl)benzoyl]cyclohexane–1,3,5–trione,--
In Claim 21, col. 40. indicated lines 17–18:
"5–methyl–2–[2–methyl–3,4–di(methylsulfonyl)benzoyl]cyclohex– ane–1,3–dione,"
should read
--5–methyl–2–[2–methyl–3,4–di(methylsulfonyl)benzoyl]cyclohexane–1,3–dione,--
In Claim 21, col. 40, indicated lines 19–20:
"4,4–dimethyl–2–[2–methyl–3,4–di(methylsulfonyl)benzoyl]cyclohex– ane–1,3–dione,"
should read
--4,4–dimethyl–2–[2–methyl–3,4–di(methylsulfonyl)benzoyl]cyclohexane–1,3–dione,--
In Claim 21, col. 40, indicated lines 21–22:
"5,5–dimethyl–2–[2–methyl–3,4–di(methylsulfonyl)benzoyl]cyclohex– ane–1,3–dione,"
should read
--5,5–dimethyl–2–[2–methyl–3,4–di(methylsulfonyl)benzoyl]cyclohexane–1,3–dione,--
In Claim 21, col. 40, indicated lines 23–24:
"2– [4–chloro–2–methyl–3–methylsulfonylbenzoyl]cyclohexane–1,3–di– one."
should read
--2–[4–chloro–2–methy–3–methylsulfonylbenzoyl]cyclohexane–1,3–dione.--
In Claim 22, col. 40, indicated lines 29–30"
"$C_1$–$C_4$–haloalkyl– thio," should read --$C_1$–$C_4$–haloalkylthio,--
In Claim 22, col. 40, indicated lines 30–31:
"$C_1$–$C_4$–haloalkylsul– finyl," should read --$C_1$–$C_4$–haloalkylsulfinyl,--
In Claim 23, col. 40, indicated line 36:
"$C_1$–$C_4$–alkyl" should read --$C_1$–$C_4$–alkyl;--
In Claim 23, col. 40, indicated lines 38–39:
"$C_1$–$C_4$–haloalkyl– thio," should read --$C_1$–$C_4$–haloalkylthio,--

UNITED STATES PATENT AND TRADEMARK OFFICE
CERTIFICATE OF CORRECTION

PATENT NO. : 7,196,229 B2
APPLICATION NO. : 10/485922
DATED : March 27, 2007
INVENTOR(S) : von Deyn et al.

It is certified that error appears in the above-identified patent and that said Letters Patent is hereby corrected as shown below:

In Claim 23, col. 40, indicated lines 39–40:
"$C_1$–$C_4$–haloalkylsul– finyl," should read --$C_1$–$C_4$–haloalkylsulfinyl,--

Signed and Sealed this

Twenty-fourth Day of July, 2007

JON W. DUDAS
*Director of the United States Patent and Trademark Office*